United States Patent [19]
Schnepf et al.

[11] Patent Number: 6,166,195
[45] Date of Patent: *Dec. 26, 2000

[54] NEMATODE-ACTIVE TOXINS AND GENES WHICH CODE THEREFOR

[75] Inventors: H. Ernest Schnepf, San Diego; George E. Schwab, La Jolla; Jewel Payne, Davis; Kenneth E. Narva, San Diego; Luis Foncerrada, Vista, all of Calif.

[73] Assignee: Mycogen Corporation, San Diego, Calif.

[ * ] Notice: This patent is subject to a terminal disclaimer.

[21] Appl. No.: 09/076,137

[22] Filed: May 12, 1998

Related U.S. Application Data

[62] Division of application No. 08/316,301, Sep. 30, 1994, Pat. No. 5,753,492, which is a division of application No. 07/871,510, Apr. 23, 1992, abandoned, which is a continuation-in-part of application No. 07/830,050, Jan. 31, 1992, abandoned, which is a continuation-in-part of application No. 07/693,018, May 3, 1991, abandoned, said application No. 07/693,018, is a continuation-in-part of application No. 07/565,544, Aug. 10, 1990, abandoned, which is a continuation-in-part of application No. 07/084,653, Aug. 12, 1987, Pat. No. 4,948,734.

[51] Int. Cl.[7] ...................................................... C07H 21/04
[52] U.S. Cl. ...................................... 536/24.33; 536/23.71
[58] Field of Search ............................. 435/252.3; 514/2, 514/12; 536/23.1, 23.71, 24.33

[56] References Cited

U.S. PATENT DOCUMENTS

| | | | |
|---|---|---|---|
| 4,948,734 | 8/1990 | Edwards et al. | 514/2 |
| 5,281,530 | 1/1994 | Sick et al. | 435/252.3 |
| 5,426,049 | 6/1995 | Sick et al. | 435/252.3 |
| 5,753,492 | 5/1998 | Schnepf et al. | 435/252.3 |

OTHER PUBLICATIONS

Prichard, R.K. et al. (1980) "The Problem of Anthelmintic Resistance in Nematodes" Australian Veterinary Journal 56:239–251.

Coles, G.C. (1986) "Anthelmintic Resistance in Sheep" Veterinary Clinics of North America: Food Animal Practice 2(2):423–432.

Bottjer, K.P., L.W. Bone, S.S. Gill (1985) "Nematoda: Susceptibility of the Egg to *Bacillus thuringiensis* Toxins" Experimental Parasitology 60:239–244.

Ignoffo, C.M., V.H. Dropkin (1977) "Deleterious Effects of the Thermostable Toxin of *Bacillus thuringiensis* on Species of Soil–Inhabiting, Myceliophagus, and Plant–Parasitic Nematodes" Journal of the Kansas Entomological Society 50(3):394–398.

Ciordia, H., W.E. Bizzell (1961) "A Preliminary Report on the Effects of *Bacillus thuringiensis* var. thuringiensis Berliner on the Development of the Free–Living Stages of Some Cattle Nematodes" Journal of Parasitology 47:41, Abstract No. 86.

Hofte, H., H.R. Whiteley (1989) Insecticidal Crystal Proteins of *Bacillus thuringiensis* Microbiological Reviews 53(2):242–255.

Suggs, S.V., et al. (1981) "Use of Synthetic Oligonucleotides as Hybridization Probes: Isolation of Cloned cDNA Sequences for Human $\beta_2$–microglobulin" Proc. Natl. Acad. Sci. USA 78(11):6613–6617.

Prefontaine, G., et al. (1987) "Use of Oligonucleotide Probes to Study the Relatedness of Delta–Endotoxin Genes among *Bacillus thuringiensis* Subspecies and Strains"Applied and Environmental Microbiology 53(12):2808–2814.

Haider, M.Z., et al. (1987) "Cloning and Heterologous Expression of an Insecticidal Delta–Endotoxin Gene from *Bacillus thuringiensis* var. aizawai IC1 Toxic to both Lepidoptera and Diptera" Gene 52:285–290.

*Primary Examiner*—Christopher S. F. Low
*Assistant Examiner*—Davesh Srivastava
*Attorney, Agent, or Firm*—Saliwanchik, LLoyd & Saliwanchik

[57] ABSTRACT

This invention concerns genes or gene fragments which have been cloned from novel *Bacillus thuringiensis* isolates which have nematicidal activity. These genes or gene fragments can be used to transform suitable hosts for controlling nematodes.

16 Claims, No Drawings

NEMATODE-ACTIVE TOXINS AND GENES WHICH CODE THEREFOR

CROSS-REFERENCE TO A RELATED APPLICATION

This is a division of application Ser. No. 08/316,301 filed on Sep. 30, 1994, now Pat. No. 5,753,492 which is a division of application Ser. No. 07/871,510, filed on Apr. 23, 1992 now abandoned; which is a continuation-in-part of application Ser. No. 07/693,018, filed on May 3, 1991, now abandoned, and a continuation-in-part of application Ser. No. 07/830,050, filed on Jan. 31, 1992, now abandoned; Ser. No. 07/693,018 was a continuation-in-part of Ser. No. 07/565,544, filed on Aug. 10, 1990, now abandoned; which is a continuation-in-part of application Ser. No. 07/084,653, filed on Aug. 12, 1987, now U.S. Pat. No. 4,948,734.

BACKGROUND OF THE INVENTION

Regular use of chemicals to control unwanted organisms can select for chemical resistant strains. This has occurred in many species of economically important insects and has also occurred in nematodes of sheep, goats, and horses. The development of chemical resistance necessitates a continuing search for new control agents having different modes of action.

In recent times, the accepted methodology for control of nematodes has centered around the drug benzimidazole and its congeners. The use of these drugs on a wide scale has led to many instances of resistance among nematode populations (Prichard, R. K. et al. [1980] "The problem of anthelmintic resistance in nematodes," Austr. Vet. J. 56:239–251; Coles, G. C. [1986] "Anthelmintic resistance in sheep," In *Veterinary Clinics of North America: Food Animal Practice*, Vol 2:423–432 [Herd, R. P., eds.] W. B. Saunders, New York). There are more than 100,000 described species of nematodes.

The bacterium *Bacillus thuringiensis* (*B.t.*) produces a δ-endotoxin polypeptide that has been shown to have activity against a rapidly growing number of insect species. The earlier observations of toxicity only against lepidopteran insects have been expanded with descriptions of *B.t.* isolates with toxicity to dipteran and coleopteran insects. These toxins are deposited as crystalline inclusions within the organism. Many strains of *B.t.* produce crystalline inclusions with no demonstrated toxicity to any insect tested.

A small number of research articles have been published about the effects of delta endotoxins from *B. thuringiensis* species on the viability of nematode eggs. Bottjer, Bone and Gill (Experimental Parasitology 60:239–244, 1985) have reported that *B.t. kurstaki* and *B.t. israelensis* were toxic in vitro to eggs of the nematode *Trichostrongylus colubriformis*. In addition, 28 other *B.t.* strains were tested with widely variable toxicities. The most potent had $LD_{50}$ values in the nanogram range. Ignoffo and Dropkin (Ignoffo, C. M. and Dropkin, V. H. [1977] J. Kans. Entomol. Soc. 50:394–398) have reported that the thermostable toxin from *Bacillus thuringiensis* (beta exotoxin) was active against a free-living nematode, *Panagrellus redivivus* (Goodey); a plant-parasitic nematode, *Meloidogyne incognita* (Chitwood); and a fungus-feeding nematode, *Aphelenchus avena* (Bastien). Beta exotoxin is a generalized cytotoxic agent with little or no specificity. Also, H. Ciordia and W. E. Bizzell (Jour. of Parasitology 47:41 [abstract] 1961) gave a preliminary report on the effects of *B. thuringiensis* on some cattle nematodes.

At the present time there is a need to have more effective means to control the many nematodes that cause considerable damage to susceptible hosts. Advantageously, such effective means would employ biological agents.

BRIEF SUMMARY OF THE INVENTION

The subject invention concerns novel toxins active against nematodes. A further aspect of the invention concerns genes coding for nematicidal toxins. The subject invention provides the person skilled in this art with a vast array of nematicidal toxins, methods for using these toxins, and genes that code for the toxins.

One aspect of the invention is the discovery of two generalized chemical formulae common to a wide range of nematicidal toxins. These formulae can be used by those skilled in this art to obtain and identify a wide variety of toxins having the desired nematicidal activity. The subject invention concerns other teachings which enable the skilled practitioner to identify and isolate nematode active toxins and the genes which code therefor. For example, characteristic features of nematode-active toxin crystals are disclosed herein. Furthermore, characteristic levels of amino acid homology can be used to characterize the toxins of the subject invention. Yet another characterizing feature pertains to immunoreactivity with certain antibodies. Also, nucleotide probes specific for genes encoding toxins with nematicidal activity are described.

In addition to the teachings of the subject invention which define groups of *B.t.* toxins with advantageous nematicidal activity, a further aspect of the subject invention is the provision of specific nematicidal toxins and the nucleotide sequences which code for these toxins.

One aspect of the of the subject invention is the discovery of two groups of *B.t.*-derived nematode-active toxins. One group (CryV) is exemplified by the gene expression products of PS 17, PS33F2 and PS63B, while the other group (CryVI) is exemplified by the gene expression products of PS52A1 and PS69D1. The organization of the toxins within each of the two groups can be accomplished by sequence-specific motifs, overall sequence similarity, immunoreactivity, and ability to hybridize with specific probes.

The genes or gene fragments of the invention encode *Bacillus thuringiensis* δ-endotoxins which have nematicidal activity. The genes or gene fragments can be transferred to suitable hosts via a recombinant DNA vector.

BRIEF DESCRIPTION OF THE SEQUENCES

SEQ ID NO. 1 discloses the DNA of 17a.

SEQ ID NO. 2 discloses the amino acid sequence of the toxin encoded by 17a.

SEQ ID NO. 3 discloses the DNA of 17b.

SEQ ID NO. 4 discloses the amino acid sequence of the toxin encoded by 17b.

SEQ ID NO. 5 is the nucleotide sequence of a gene from 33F2.

SEQ ID NO. 6 is the amino acid sequence of the protein expressed by the gene from 33F2.

SEQ ID NO. 7 is the nucleotide sequence of a gene from 52A1.

SEQ ID NO. 8 is the amino acid sequence of the protein expressed by the gene from 52A1.

SEQ ID NO. 9 is the nucleotide sequence of a gene from 69D1.

SEQ ID NO. 10 is the amino acid sequence of the protein expressed by the gene from 69D1.

SEQ ID NO. 11 is the nucleotide sequence of a gene from 63B.

SEQ ID NO. 12 is the amino acid sequence of the protein expressed by the gene from 63B.

SEQ ID NO. 13 is the amino acid sequence of a probe which can be used according to the subject invention.

SEQ ID NO. 14 is the DNA coding for the amino acid sequence of SEQ ID NO. 13.

SEQ ID NO. 15 is the amino acid sequence of a probe which can be used according to the subject invention.

SEQ ID NO. 16 is the DNA coding for the amino acid sequence of SEQ ID NO. 15.

SEQ ID NO. 17 is the N-terminal amino acid sequence of 17a.

SEQ ID NO. 18 is the N-terminal amino acid sequence of 17b.

SEQ ID NO. 19 is the N-terminal amino acid sequence of 52A1.

SEQ ID NO. 20 is the N-terminal amino acid sequence of 63B.

SEQ ID NO. 21 is the N-terminal amino acid sequence of 69D1.

SEQ ID NO. 22 is the N-terminal amino acid sequence of 33F2.

SEQ ID NO. 23 is an internal amino acid sequence for 63B.

SEQ ID NO. 24 is a synthetic oligonucleotide derived from 17.

SEQ ID NO. 25 is an oligonucleotide probe designed from the N-terminal amino acid sequence of 52A1.

SEQ ID NO. 26 is the synthetic oligonucleotide probe designated as 69D1-D.

SEQ ID NO. 27 is the forward oligonucleotide primer from 63B.

SEQ ID NO. 28 is the reverse oligonucleotide primer from 63B.

SEQ ID NO. 29 is the nematode (NEMI) variant of region 5 of Höfte and Whiteley.

SEQ ID NO. 30 is the reverse complement primer to SEQ ID NO. 29, used according to the subject invention.

SEQ ID NO. 31 is a peptide for designing a reverse oligonucleotide primer used according to the subject invention.

SEQ ID NO. 32 is the DNA coding for the primer of SEQ ID NO. 31.

SEQ ID NO. 33 is oligonucleotide probe 33F2A.

SEQ ID NO. 34 is oligonucleotide probe 33F2B.

SEQ ID NO. 35 is a reverse primer used according to the subject invention.

SEQ ID NO. 36 is a forward primer according to the subject invention.

SEQ ID NO. 37 is a probe according to the subject invention.

SEQ ID NO. 38 is a probe according to the subject invention.

SEQ ID NO. 39 is a probe according to the subject invention.

SEQ ID NO. 40 is a forward primer according to the subject invention.

SEQ ID NO. 41 is Generic Formula I in PATENTIN format.

SEQ ID NO. 42 is Generic Formula II in PATENTIN format.

DETAILED DISCLOSURE OF THE INVENTION

The subject invention concerns a vast array of B.t. δ-endotoxins having nematicidal activity. In addition to having nematicidal activity, the toxins of the subject invention will have one or more of the following characteristics:

1. An amino acid sequence according to either of the two generic formulae disclosed herein.
2. A high degree of amino acid homology with specific toxins disclosed herein.
3. A DNA sequence encoding the toxin which hybridizes with probes or genes disclosed herein.
4. A nucleotide sequence which can be amplified using primers disclosed herein.
5. A crystal toxin presentation as described herein.
6. Inmnunoreactivity to an antibody raised to a specific toxin disclosed herein.

One aspect of the subject invention concerns the discovery of generic chemical formulae which describe toxins having activity against nematodes. Two formulae are provided: one which pertains to nematicidal toxins having molecular weights of between about 45 kDa and 65 kDa, and the other pertains to larger nematicidal proteins having molecular weights from about 65 kDa to about 155 kDa. These formulae represent two different categories of B.t. δ-endotoxins, each of which has activity against nematodes. The formula describing smaller proteins describes many CryV proteins, while the formula describing larger proteins describes many CryVI proteins. A description of these two formulae is as follows:

Generic Formula I. This formula describes toxin proteins having molecular weights from about 65 kDa to about 155 kDa. The first 650–700 amino acids for proteins in excess of about 75 kDa and the entire molecule (for proteins of less than about 75 kDa) have substantially the following sequence (and see SEQ ID NO. 41):

```
  1 MOXXXXXXPX BPYNBLOXXP XZXXXXXXXX
    OXXXBXXXEUXBKXBJJXX       XOxxxxZXXZ
    xXOBXJXBJX XBXXXXBXYX XXVUXXZLZLB
    xxxXXOBPXB
101 ZBXXPBLZBB BXXBXXXXOx xxXUXOXLBX
    XBOXXBUJBLDJXLXXXXXX XLUXELXXBX X
    LXXKXXXXB XExxBXXHXX BXXBXXZXXX
    KBXXXXBZXX
201 ZBXOXXBXXB LOEXXXJxxx LXBPXYXBXO
    XMXLXXXXXX LXXZXOWXXK BxxxxxxxxX
    XXXXOLXXXK XXBKXXLXBY XXXXXXBBXX
    XLXZXZxxZX
301 XXXBXJXXXY XJXMXXX*LEE BXXXXPOBXP
    EXYxxxZZXL XLXKOKXLBZ XBBXXXXXxx
    XZBOLXUXXX XOXXXXXXXX ZXXXBXXXXJ
    JBXKxUBKBY
401 XXXXXXX*XX *Bx*YXXXBX BUXXXXOXXY
    ZXxxxXEPXX ZXXxxxBXXX XPBXXBUXXO
    XXOXXXXXXX XXOXXXKZXB *XLxxxxxxx
    *BXXKX*XXX
501 ZXZXZXZ*XX XLXZXXXXXX XXXXXXXXXX
    XZXXXxxxxx XLBXXXXPXE XXXXUXLZXX
    EXXZxUBXXX ZBPBEKxxOZ XXXXBxxBKE
    WLUZOXXXXL
601 ZPZUZXZBXB OUXOZZXYXB RCRYOZXXXO
    XBBBUxBXXZ ZXUPLXXUYBX BXXOXEXXOX
```

XXXXUXBXXB KZLXXXXXXB xxxxXxJLPX
XXBXBXBOUX
701 ZSSXBXLDKL EBBPBX
Numbering is for convenience and approximate location only.

| A = ala | G = gly | M = met | S = ser |
|---------|---------|---------|---------|
| C = cys | H = his | N = asn | T = thr |
| D = asp | I = ile | P = pro | V = val |
| E = glu | K = lys | Q = gln | W = trp |
| F = phe | L = leu | R = arg | Y = tyr |

K = K or R
E = E or D
L = L or I
B = M, L, I, V, or F
J = K, R, E, or D
O = A or T
U = N or Q
Z = G or S
X = any naturally occurring amino acid, except C.
* = any naturally occurring amino acid.
x = any naturally occurring amino acid, except C (or complete omission of any amino acids).

Where a stretch of wild-card amino acids are encountered (X(n) or x(n) where n>2), repetition of a given amino acid should be avoided. Similarly, P, C, E, D, K, or R utilization should be minimized.

This formula (hereinafter referred to as Generic Formula I) is exemplified in the current application by the specific toxins 17a, 17b and 63b.

Generic Formula II. This formula describes toxin proteins having molecular weights from about 45 kDa to about 65 kDa. Their primary amino acid structure substantially follows the motif illustrated below (and see SEQ NO: 42):

1 MLBXXXXOBP KHxxxXXXXO XXXXZXKKxx
  xXZPXXBXXX XXBLLZKXEW OXBXOYBXOZ
  XZLPBUJXXB KXHBXLXXJL XLPXJBXULY
  JBYXXJKXXX
  ΦXWWUXXLXPL BBKXOUJLXX YZBKXOZJXX K
  KxxZXXJXB UJJBJULXJU XXJJOXXXKO X
  KJBXOKCXL LLKEOJUYJX OOJXBXXXLX XB
  LXZXUxxx
201 xXJBXZBXXB UXXLXXBXXX LXXXXZJXZP
    XXJELLJKBJ XLKXXLEXXL KOEUJLEKKB
    BXZBXLZPLL ZBBBYELLEX OOBXXLXXXB JX
    LXXXLJXO
301 UXJLJKJBKL LZBBUZLXOJ LJXBXXUZXX O
    LXBBXKLXZ LWXXLXXULX ULKXOZXXEB
    XJXXJXJXLX LELXJOXXXW XXBOXEOXXB X
    LUZYXXxx
401 (x)n$^a$
   $^a$Where n=0–100

The symbols used for this formula are the same as those used for Generic Formula I.

This formula (hereinafter referred to as Generic Formula II) is exemplified in the current application by specific toxins 52A1 and 69D1.

Nematode-active toxins according to the formulae of the subject invention are specifically exemplified herein by the toxins encoded by the genes designated 17a, 17b, 63B, 52A1, and 69D1. Since these toxins are merely exemplary of the toxins represented by the generic formulae presented herein, it should be readily apparent that the subject invention further comprises equivalent toxins (and nucleotide sequences coding for equivalent toxins) having the same or similar biological activity of the specific toxins disclosed or claimed herein. These equivalent toxins will have amino acid homology with the toxins disclosed and claimed herein. This amino acid homology will typically be greater than 50%, preferably be greater than 75%, and most preferably be greater than 90%. The amino acid homology will be highest in certain critical regions of the toxin which account for biological activity or are involved in the determination of three-dimensional configuration which ultimately is responsible for the biological activity. In this regard, certain amino acid substitutions are acceptable and can be expected if these substitutions are in regions which are not critical to activity or are conservative amino acid substitutions which do not affect the three-dimensional configuration of the molecule. For example, amino acids may be placed in the following classes: non-polar, uncharged polar, basic, and acidic. Conservative substitutions whereby an amino acid of one class is replaced with another amino acid of the same type fall within the scope of the subject invention so long as the substitution does not materially alter the biological activity of the compound. Table 1 provides a listing of examples of amino acids belonging to each class.

TABLE 1

| Class of Amino Acid | Examples of Amino Acids |
|---------------------|-------------------------|
| Nonpolar | Ala, Val, Leu, Ile, Pro, Met, Phe, Trp |
| Uncharged Polar | Gly, Ser, Thr, Cys, Tyr, Asn, Gln |
| Acidic | Asp, Glu |
| Basic | Lys, Arg, His |

In some instances, non-conservative substitutions can also be made. The critical factor is that these substitutions must not significantly detract from the biological activity of the toxin. The information presented in the generic formulae of the subject invention provides clear guidance to the person skilled in this art in making various amino acid substitutions.

Further guidance for characterizing the nematicidal toxins of the subject invention is provided in Tables 3 and 4, which demonstrate the relatedness among toxins within each of the above-noted groups of nematicidal toxins (CryV and CryVI). These tables show a numeric score for the best matching alignment between two proteins that reflects: (1) positive scores for exact matches, (2) positive or negative scores reflecting the likelihood (or not) of one amino acid substituting for another in a related protein, and (3) negative scores for the introduction of gaps. A protein sequence aligned to itself will have the highest possible score-i.e., all exact matches and no gaps. However, an unrelated protein or a randomly generated sequence will typically have a low positive score. Related sequences have scores between the random background score and the perfect match score.

The sequence comparisons were made using the algorithm of Smith and Waterman ([1981] Advances in Applied Mathematics 2:482–489), implemented as the program "Bestfit" in the GCG Sequence Analysis Software Package Version 7 April 1991. The sequences were compared with default parameter values (comparison table: Swgappep.Cmp, Gap weight:3.0, Length weight:0.1) except that gap limits of 175 residues were applied to each sequence compared. The program output value compared is referred to as the Quality score.

Tables 3 and 4 show the pairwise alignments between the indicated amino acids of the two classes of nematode-active proteins CryV and CryVI and representatives of dipteran (CryIV; Sen, K. et al. [1988] Agric. Biol. Chem. 52:873–878), lepidopteran and dipteran (CryIIA; Widner and Whiteley [1989] J. Bacteriol. 171:965–974), lepidopteran (CryIA(c); Adang et al. [1981] Gene 36:289–300), and coleopteran (CryIIIA; Herrnstadt et al. [1987] Gene 57:37–46) proteins.

Table 2 shows which amino acids were compared from the proteins of interest.

TABLE 2

| Protein | Amino acids compared |
| --- | --- |
| 63B | 1-692 |
| 33F2 | 1-618 |
| 17a | 1-677 |
| 17b | 1-678 |
| CryIV | 1-633 |
| CryIIA | 1-633 |
| CryIA(c) | 1-609 |
| CryIIIA | 1-644 |
| 69D1 | 1-395 |
| 52A1 | 1-475 |

Table 3 shows the scores prior to adjustment for random sequence scores.

TABLE 3

|  | 63B | 33F2 | 17a | CryIVA | CryIIA | CryIA(c) | CryIIIA | 52A1 | 69D1 |
| --- | --- | --- | --- | --- | --- | --- | --- | --- | --- |
| 63B | 1038 | 274 | 338 | 235 | 228 | 232 | 244 | 154 | 122 |
| 33F2 |  | 927 | 322 | 251 | 232 | 251 | 270 | 157 | 130 |
| 17a |  |  | 1016 | 240 | 240 | 237 | 249 | 152 | 127 |
| CryIVA |  |  |  | 950 | 245 | 325 | 326 | 158 | 125 |
| CryIIA |  |  |  |  | 950 | 244 | 241 | 151 | 132 |
| CryIA(c) |  |  |  |  |  | 914 | 367 | 151 | 127 |
| CryIIIA |  |  |  |  |  |  | 966 | 150 | 123 |
| 52A1 |  |  |  |  |  |  |  | 713 | 350 |
| 69D1 |  |  |  |  |  |  |  |  | 593 |

Note that for each nematode-active protein, the highest score is always with another nematode-active protein. For example, 63B's highest score, aside from itself, is with 17a.

Furthermore, 33F2's highest score, aside from itself, is also with 17a. Similarly, 52A1 and 69D1 have a higher score versus each other than with the other proteins.

Table 4 shows the same analysis after subtraction of the average score of 50 alignments of random shuffles of the column sequences with the row sequences.

TABLE 4

|  | 63B | 33F2 | 17a | CryIVA | CryIIA | CryIA(c) | CryIIIA | 52A1 | 69D1 |
| --- | --- | --- | --- | --- | --- | --- | --- | --- | --- |
| 63B | 830 | 81 | 130 | 40 | 32 | 42 | 48. | 0.1 | −8.8 |
| 33F2 |  | 740 | 128 | 66 | 48 | 72 | 85 | 1.4 | −2.9 |
| 17a |  |  | 808 | 45 | 45 | 45 | 54 | −0.8 | −5.2 |
| CryIVA |  |  |  | 759 | 54 | 142 | 138 | 5.4 | −4.1 |
| CryIIA |  |  |  |  | 755 | 58 | 53 | −2.3 | 6 |
| CryIA(c) |  |  |  |  |  | 728 | 185 | 3.1 | 0 |
| CryIIIA |  |  |  |  |  |  | 766 | −2.3 | 6.9 |
| 52A1 |  |  |  |  |  |  |  | 566 | 221 |
| 69D1 |  |  |  |  |  |  |  |  | 465 |

Note that in Table 4 the same relationships hold as in Table 3, i.e., 63B's highest score, aside from itself, is with 17a, and 33F2's highest score, aside from itself, is also with 17a.

Similarly, 52A1 and 69D1 have a better score versus each other than with the other proteins.

Thus, certain toxins according to the subject invention can be defined as those which have nematode activity and either have an alignment value (according to the procedures of Table 4) greater than 100 with 17a or have an alignment value greater than 100 with 52A1. As used herein, the term "alignment value" refers to the scores obtained above and used to create the scores reported in Table 4.

The toxins of the subject invention can also be characterized in terms of the shape and location of crystal toxin inclusions. Specifically, nematode-active inclusions typically remain attached to the spore after cell lysis. These inclusions are not inside the exosporium, as in previous descriptions of attached inclusions, but are held within the spore by another mechanism. Inclusions of the nematode-active isolates are typically amorphic, generally long and/or multiple. These inclusions are distinguishable from the larger round/amorphic inclusions that remain attached to the spore. No B.t. strains that fit this description have been found to have activity against the conventional targets- Lepidoptera, Diptera, or Colorado Potato Beetle. Alf nematode-active strains fit this description except one. Thus, there is a very high correlation between this crystal structure and nematode activity.

The genes and toxins according to the subject invention include not only the full length sequences disclosed herein but also fragments of these sequences, or fusion proteins, which retain the characteristic nematicidal activity of the sequences specifically exemplified herein.

It should be apparent to a person skilled in this art that genes coding for nematode-active toxins can be identified and obtained through several means. The specific genes may be obtained from a culture depository as described below. These genes, or portions thereof, may be constructed synthetically, for example, by use of a gene machine.

Variations of these genes may be readily constructed using standard techniques for making point mutations. Also, fragments of these genes can be made using commercially available exonucleases or endonucleases according to standard procedures. For example, enzymes such as Bal31 or site-directed mutagenesis can be used to systematically cut off nucleotides from the ends of these genes. Also, genes which code for active fragments may be obtained using a variety of other restriction enzymes. Proteases may be used to directly obtain active fragments of these toxins.

Equivalent toxins and/or genes encoding these equivalent toxins can also be located from B.t. isolates and/or DNA libraries using the teachings provided herein. There are a number of methods for obtaining the nematode-active toxins of the instant invention which occur in nature. For example, antibodies to the nematode-active toxins disclosed and claimed herein can be used to identify and isolate other toxins from a mixture of proteins. Specifically, antibodies may be raised to the portions of the nematode-active toxins which are most constant and most distinct from other B.t. toxins. These antibodies can then be used to specifically identify equivalent toxins with the characteristic nematicidal activity by immunoprecipitation, enzyme linked immunoassay (ELISA), or Western blotting. Antibodies to the toxins disclosed herein, or to equivalent toxins, or fragments of these toxins, can readily be prepared using standard procedures in this art. The genes coding for these toxins can then be obtained from the microorganism.

A further method for identifying the toxins and genes of the subject invention is through the use of oligonucleotide probes. These probes are nucleotide sequences having a detectable label. As is well known in the art, if the probe molecule and nucleic acid sample hybridize by forming a strong bond between the two molecules, it can be reasonably assumed that the probe and sample are essentially identical. The probe's detectable label provides a means for determining in a known manner whether hybridization has occurred. Such a probe analysis provides a rapid method for identifying nematicidal endotoxin genes of the subject invention.

The nucleotide segments which are used as probes according to the invention can be synthesized by use of DNA synthesizers using standard procedures. In the use of the nucleotide segments as probes, the particular probe is labeled with any suitable label known to those skilled in the art, including radioactive and non-radioactive labels. Typical radioactive labels include $^{32}P$, $^{125}I$, 35S, or the like. A probe labeled with a radioactive isotope can be constructed from a nucleotide sequence complementary to the DNA sample by a conventional nick translation reaction, using a DNase and DNA polymerase. The probe and sample can then be combined in a hybridization buffer solution and held at an appropriate temperature until annealing occurs. Thereafter, the membrane is washed free of extraneous materials, leaving the sample and bound probe molecules typically detected and quantified by autoradiography and/or liquid scintillation counting.

Non-radioactive labels include, for example, ligands such as biotin or thyroxine, as well as enzymes such as hydrolases or perioxidases, or the various chemiluminescers such as luciferin, or fluorescent compounds like fluorescein and its derivatives. The probe may also be labeled at both ends with different types of labels for ease of separation, as, for example, by using an isotopic label at the end mentioned above and a biotin label at the other end.

Duplex formation and stability depend on substantial complementarity between the two strands of a hybrid, and, as noted above, a certain degree of mismatch can be tolerated. Therefore, the probes of the subject invention include mutations (both single and multiple), deletions, insertions of the described sequences, and combinations thereof, wherein said mutations, insertions and deletions permit formation of stable hybrids with the target polynucleotide of interest. Mutations, insertions, and deletions can be produced in a given polynucleotide sequence in many ways, and these methods are known to an ordinarily skilled artisan. Other methods may become known in the future.

The known methods include, but are not limited to:

(1) synthesizing chemically or otherwise an artificial sequence which is a mutation, insertion or deletion of the known sequence;

(2) using a probe of the present invention to obtain via hybridization a new sequence or a mutation, insertion or deletion of the probe sequence; and (3) mutating, inserting or deleting a test sequence in vitro or in vivo.

It is important to note that the mutational, insertional, and deletional variants generated from a given probe may be more or less efficient than the original probe. Notwithstanding such differences in efficiency, these variants are within the scope of the present invention.

Thus, mutational, insertional, and deletional variants of the disclosed test sequences can be readily prepared by methods which are well known to those skilled in the art. These variants can be used in the same manner as the instant probes so long as the variants have substantial sequence homology with the probes. As used herein, substantial sequence homology refers to homology which is sufficient to enable the variant to function in the same capacity as the original probe. Preferably, this homology is greater than 50%; more preferably, this homology is greater than 75%; and most preferably, this homology is greater than 90%. The degree of homology needed for the variant to function in its intended capacity will depend upon the intended use of the sequence. It is well within the skill of a person trained in this art to make mutational, insertional, and deletional mutations which are designed to improve the function of the sequence or otherwise provide a methodological advantage.

Specific nucleotide probes useful, according to the subject invention, in the rapid identification of nematode-active genes are (i) DNA coding for a peptide sequence whose single letter amino acid designation is "REWINGAN" (SEQ ID NO. 13) or variations thereof which embody point mutations according to the following: position 1, R or P or K;

position 3, W or Y; position 4, I or L; position 8, N or P; a specific example of such a probe is "AGA(A or G)T(G or A)(G or T)(A or T)T(A or T)AATGG(A or T)GC(G or T)(A or C)A(A or T)" (SEQ ID NO. 14);

(ii) DNA coding for a peptide sequence whose single letter amino acid designation is "PTFDPDLY" (SEQ ID NO. 15) or variations thereof which embody point mutations according to the following: position 3, F or L;

position 4, D or Y; position 7, L or H or D; a specific example of such a probe is "CC(A or T)AC(C or T)TTT(T or G)ATCCAGAT(C or G)(T or A)(T or C)TAT" (SEQ ID NO. 16).

The potential variations in the probes listed is due, in part, to the redundancy of the genetic code. Because of the redundancy of the genetic code, i.e., more than one coding nucleotide triplet (codon) can be used for most of the amino acids used to make proteins. Therefore different nucleotide sequences can code for a particular amino acid. Thus, the amino acid sequences of the B.t. toxins and peptides can be prepared by equivalent nucleotide sequences encoding the same amino acid sequence of the protein or peptide. Accordingly, the subject invention includes such equivalent nucleotide sequences. Also, inverse or complement sequences are an aspect of the subject invention and can be readily used by a person skilled in this art. In addition it has been shown that proteins of identified structure and function may be constructed by changing the amino acid sequence if such changes do not alter the protein secondary structure (Kaiser, E. T. and Kezdy, F. J. [1984] Science 223:249–255). Thus, the subject invention includes mutants of the amino acid sequence depicted herein which do not alter the protein secondary structure, or if the structure is altered, the biological activity is substantially retained. Further, the invention also includes mutants of organisms hosting all or part of a toxin encoding a gene of the invention. Such microbial mutants can be made by techniques well known to persons skilled in the art. For example, UV irradiation can be used to prepare mutants of host organisms. Likewise, such mutants may include asporogenous host cells which also can be prepared by procedures well known in the art.

The toxin genes or gene fragments exemplified according to the subject invention can be obtained from nematode-active *B. thuringiensis* (*B.t.*) isolates designated PS17, PS33F2, PS63B, PS52A1, and PS69D1. Subcultures of the *E. coli* host harboring the toxin genes of the invention were deposited in the permanent collection of the Northern Research Laboratory, U.S. Department of Agriculture, Peoria, Ill., USA. The accession numbers are as follows:

| Culture | Repository No. | Deposit Date |
|---|---|---|
| B.t. isolate PS17 | NRRL B-18243 | July 28, 1987 |
| B.t. isolate PS33F2 | NRRL B-18244 | July 28, 1987 |
| B.t. isolate PS63B | NRRL B-18246 | July 28, 1987 |
| B.t. isolate PS52A1 | NRRL B-18245 | July 28, 1987 |
| B.t. isolate PS69D1 | NRRL B-18247 | July 28, 1987 |
| E. coli NM522(pMYC 2316) | NRRL B-18785 | March 15, 1991 |
| E. coli NM522(pMYC 2321) | NRRL B-18770 | February 14, 1991 |
| E. coli NM522(pMYC 2317) | NRRL B-18816 | April 24,1991 |
| E. coli NM522(pMYC 1627) | NRRL B-18651 | May 11, 1990 |
| E. coli NM522(pMYC 1628) | NRRL B-18652 | May 11, 1990 |
| E. coli NM522(pMYC 1642) | NRRL B-18961 | April 10, 1992 |

The subject cultures have been deposited under conditions that assure that access to the cultures will be available during the pendency of this patent application to one determined by the Commissioner of Patents and Trademarks to be entitled thereto under 37 CFR 1.14 and 35 USC 122. The deposits are available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject culture deposits will be stored and made available to the public in accord with the provisions of the Budapest Treaty for the Deposit of Microorganisms, i.e., they will be stored with all the care necessary to keep them viable and uncontaminated for a period of at least five years after the most recent request for the furnishing of a sample of the deposit, and in any case, for a period of at least 30 (thirty) years after the date of deposit or for the enforceable life of any patent which may issue disclosing the cultures. The depositor acknowledges the duty to replace the deposits should the depository be unable to furnish a sample when requested, due to the condition of the deposit(s). All restrictions on the availability to the public of the subject culture deposits will be irrevocably removed upon the granting of a patent disclosing them.

The novel *B.t.* genes or gene fragments of the invention encode toxins which show activity against tested nematodes. The group of diseases described generally as helminthiasis is due to infection of an animal host with parasitic worms known as helminths. Helminthiasis is a prevalent and serious economic problem in domesticated animals such as swine, sheep, horses, cattle, goats, dogs, cats and poultry.

Among the helminths, the group of worms described as nematodes causes wide-spread and often times serious infection in various species of animals. The most common genera of nematodes infecting the animals referred to above are Haemonchus, Trichostrongylus, Ostertagia, Nematodirus, Cooperia, Ascaris, Bunostomum, Oesophagostomum, Chabertia, Trichuris, Strongylus, Trichonema, Dictyocaulus, Capillaria, Heterakis, Toxocara, Ascaridia, Oxyuris, Ancylostoma, Uncinaria, Toxascaris, Caenorhabditis and Parascaris. Certain of these, such as Nematodirus, Cooperia, and Oesophagostomum, attack primarily the intestinal tract, while others, such as Dictyocaulus are found in the lungs. Still other parasites may be located in other tissues and organs of the body.

The toxins encoded by the novel *B.t.* genes of the invention are useful as nematicides for the control of soil nematodes and plant parasites selected from the genera Bursaphalenchus, Criconemella, Ditylenchus, Globodera, Helicotylenchius, Heterodera, Melodoigyne, Pratylenchus, Radolpholus, Rotelynchus, or Tylenchus.

Alternatively, because some plant parasitic nematodes are obligate parasites, genes coding for nematicidal *B.t.* toxins can be engineered into plant cells to yield nematode-resistant plants. The methodology for engineering plant cells is well established (cf. Nester, E. W., Gordon, M. P., Amasino, R. M. and Yanofsky, M. F., Ann. Rev. Plant Physiol. 35:387–399, 1984).

The *B.t.* toxins of the invention can be administered orally in a unit dosage form such as a capsule, bolus or tablet, or as a liquid drench when used as an anthelmintic in mammals, and in the soil to control plant nematodes. The drench is normally a solution, suspension or dispersion of the active ingredient, usually in water, together with a suspending agent such as bentonite and a wetting agent or like excipient. Generally, the drenches also contain an antifoaming agent. Drench formulations generally contain from about 0.001 to 0.5% by weight of the active compound. Preferred drench formulations may contain from 0.01 to 0.1% by weight, the capsules and boluses comprise the active ingredient admixed with a carrier vehicle such as starch, talc, magnesium stearate, or dicalcium phosphate.

Where it is desired to administer the toxin compounds in a dry, solid unit dosage form, capsules, boluses or tablets containing the desired amount of active compound usually are employed. These dosage forms are prepared by intimately and uniformly mixing the active ingredient with suitable finely divided diluents, fillers, disintegrating agents and/or binders such as starch, lactose, talc, magnesium stearate, vegetable gums and the like. Such unit dosage formulations may be varied widely with respect to their total weight and content of the antiparasitic agent, depending upon the factors such as the type of host animal to be treated, the severity and type of infection and the weight of the host.

When the active compound is to be administered via an animal feedstuff, it is intimately dispersed in the feed or used as a top dressing or in the form of pellets which may then be added to the finished feed or, optionally, fed separately. Alternatively, the antiparasitic compounds may be administered to animals parenterally, for example, by intraruminal, intramuscular, intratracheal, or subcutaneous injection, in which event the active ingredient is dissolved or dispersed in a liquid carrier vehicle. For parenteral administration, the active material is suitably admixed with an acceptable vehicle, preferably of the vegetable oil variety, such as peanut oil, cotton seed oil and the like. Other parenteral vehicles, such as organic preparations using solketal, glycerol, formal and aqueous parenteral formulations, are also used. The active compound or compounds are dissolved or suspended in the parenteral formulation for administration; such formulations generally contain from 0.005 to 5% by weight of the active compound.

When the toxins are administered as a component of the feed of the animals, or dissolved or suspended in the drinking water, compositions are provided in which the active compound or compounds are intimately dispersed in an inert carrier or diluent. By inert carrier is meant one that will not react with the antiparasitic agent and one that may be administered safely to animals. Preferably, a carrier for feed administration is one that is, or may be, an ingredient of the animal ration.

Suitable compositions include feed premixes or supplements in which the active ingredient is present in relatively large amounts and which are suitable for direct feeding to the animal or for addition to the feed either directly or after an intermediate dilution or blending step. Typical carriers or diluents suitable for such compositions include, for example, distillers dried grains, corn meal, citrus meal, fermentation residues, ground oyster shells, wheat shorts, molasses solubles, corn cob meal, edible bean mill feed, soya grits, crushed limestone and the like.

The toxin genes or gene fragments of the subject invention can be introduced into a wide variety of microbial hosts. Expression of the toxin gene results, directly or indirectly, in the intracellular production and maintenance of the nematicide. With suitable hosts, e.g., Pseudomonas, the microbes can be applied to the situs of nematodes where they will proliferate and be ingested by the nematodes. The result is a control of the nematodes. Alternatively, the microbe hosting the toxin gene can be treated under conditions that prolong the activity of the toxin produced in the cell. The treated cell then can be applied to the environment of target pest(s). The resulting product retains the toxicity of the *B.t.* toxin.

Where the *B.t.* toxin gene or gene fragment is introduced via a suitable vector into a microbial host, and said host is applied to the environment in a living state, it is essential that certain host microbes be used. Microorganism hosts are selected which are known to occupy the "phytosphere" (phylloplane, phyllosphere, rhizosphere, and/or rhizoplane) of one or more crops of interest. These microorganisms are selected so as to be capable of successfully competing in the particular environment (crop and other insect habitats) with the wild-type microorganisms, provide for stable maintenance and expression of the gene expressing the polypeptide pesticide, and, desirably, provide for improved protection of the nematicide from environmental degradation and inactivation.

A large number of microorganisms are known to inhabit the phylloplane (the surface of the plant leaves) and/or the rhizosphere (the soil surrounding plant roots) of a wide variety of important crops. These microorganisms include bacteria, algae, and fungi. Of particular interest are microorganisms, such as bacteria, e.g., genera Pseudomonas, Erwinia, Serratia, Klebsiella, Xanthomonas, Streptomyces, Rhizobium, Rhodopseudomonas, Methylophilius, Agrobacterium, Acetobacter, Lactobacillus, Arthrobacter, Azotobacter, Leuconostoc, and Alcaligenes; fungi, particularly yeast, e.g., genera Saccharomyces, Cryptococcus, Kluyveromyces, Sporobolomyces, Rhodotorula, and Aureobasidium. Of particular interest are such phytosphere bacterial species as *Pseudomonas syringae, Pseudomonas fluorescens, Serratia marcescens, Acetobacter xylinum, Agrobacterium tumefaciens, Rhodopseudomonas spheroides, Xanthomonas campestris, Rhizobium melioti, Alcaligenes entrophus*, and *Azotobacter vinlandii*; and phytosphere yeast species such as *Rhodotorula rubra, R. glutinis, R. marina, R. aurantiaca, Cryptococcus albidus, C. diffluens, C. laurentii, Saccharomyces rosei, S. pretoriensis, S. cerevisiae, Sporobolomyces roseus, S. odorus, Kluyveromyces veronae*, and *Aureobasidium pollulans*. Of particular interest are the pigmented microorganisms.

A wide variety of ways are known and available for introducing the *B.t.* genes or gene fragments expressing the toxin into the microorganism host under conditions which allow for stable maintenance and expression of the gene. The transformants can be isolated in accordance with conventional ways, usually employing a selection technique, which allows for selection of the desired organism as against unmodified organisms or transferring organisms, when present. The transformants then can be tested for nematicidal activity.

Suitable host cells, where the nematicide-containing cells will be treated to prolong the activity of the toxin in the cell when the then treated cell is applied to the environment of target pest(s), may include either prokaryotes or eukaryotes, normally being limited to those cells which do not produce substances toxic to higher organisms, such as mammals. However, organisms which produce substances toxic to higher organisms could be used, where the toxin is unstable or the level of application sufficiently low as to avoid any possibility of toxicity to a mammalian host. As hosts, of particular interest will be the prokaryotes and the lower eukaryotes, such as fungi. Illustrative prokaryotes, both Gram-negative and -positive, include Enterobacteriaceae, such as Escherichia, Erwinia, Shigella, Salmonella, and Proteus; Bacillaceae; Rhizobiceae, such as Rhizobium; Spirillaceae, such as photobacterium, Zymomonas, Serratia, Aeromonas, Vibrio, Desulfovibrio, Spirillum; Lactobacillaceae; Pseudomonadaceae, such as Pseudomonas and Acetobacter; Azotobacteraceae and Nitrobacteraceae. Among eukaryotes are fungi, such as Phycomycetes and Ascomycetes, which includes yeast, such as Saccharomyces and Schizosaccharomyces; and Basidiomycetes yeast, such as Rhodotorula, Aureobasidium, Sporobolomyces, and the like.

Characteristics of particular interest in selecting a host cell for purposes of production include ease of introducing the *B.t.* gene or gene fragment into the host, availability of expression systems, efficiency of expression, stability of the nematicide in the host, and the presence of auxiliary genetic capabilities. Characteristics of interest for use as a nematicide microcapsule include protective qualities for the nematicide, such as thick cell walls, pigmentation, and intracellular packaging or formation of inclusion bodies; leaf affinity; lack of mammalian toxicity; attractiveness to pests for ingestion; ease of killing and fixing without damage to the toxin; and the like. Other considerations include ease of formulation and handling, economics, storage stability, and the like.

Host organisms of particular interest include yeast, such as Rhodotorula sp., Aureobasidium sp., Saccharomyces sp., and Sporobolomyces sp.; phylloplane organisms such as Pseudomonas sp., Erwinia sp. and Flavobacterium sp.; or such other organisms as Escherichia, Lactobacillus sp., Bacillus sp., and the like. Specific organisms include *Pseudomonas aeruginosa, Pseudomonas fluorescens, Saccharomyces cerevisiae, Bacillus thuringiensis, Escherichia coli, Bacillus subtilis*, and the like.

The cell will usually be intact and be substantially in the proliferative form when treated, rather than in a spore form, although in some instances spores may be employed.

Treatment of the microbial cell, e.g., a microbe containing the B.t. toxin gene or gene fragment, can be by chemical or physical means, or by a combination of chemical and/or physical means, so long as the technique does not deleteriously affect the properties of the toxin, nor diminish the cellular capability in protecting the toxin. Examples of chemical reagents are halogenating agents, particularly halogens of atomic no. 17–80. More particularly, iodine can be used under mild conditions and for sufficient time to achieve the desired results. Other suitable techniques include treatment with aldehydes, such as formaldehyde and glutaraldehyde; anti-infectives, such as zephiran chloride and cetylpyridinium chloride; alcohols, such as isopropyl and ethanol; various histologic fixatives, such as Bouin's fixative and Helly's fixative (See: Humason, Gretchen L., Animal Tissue Techniques, W.H. Freeman and Company, 1967); or a combination of physical (heat) and chemical agents that preserve and prolong the activity of the toxin produced in the cell when the cell is administered to the host animal. Examples of physical means are short wavelength radiation such as gamma-radiation and X-radiation, freezing, UV irradiation, lyophilization, and the like.

The cells generally will have enhanced structural stability which will enhance resistance to environmental conditions. Where the pesticide is in a proform, the method of inactivation should be selected so as not to inhibit processing of the proform to the mature form of the pesticide by the target pest pathogen. For example, formaldehyde will crosslink proteins and could inhibit processing of the proform of a polypeptide pesticide. The method of inactivation or killing retains at least a substantial portion of the bio-availability or bioactivity of the toxin.

The cellular host containing the B.t. nematicidal gene or gene fragment may be grown in any convenient nutrient medium, where the DNA construct provides a selective advantage, providing for a selective medium so that substantially all or all of the cells retain the B.t. gene or gene fragment. These cells may then be harvested in accordance with conventional ways. Alternatively, the cells can be treated prior to harvesting.

The various methods employed in the preparation of the plasrnids and transformation of host organisms are well known in the art. These procedures are all described in Maniatis, T., Fritsch, E. F., and Sambrook, J. (1982) *Molecular Cloning: A Laboratory Manual*, Cold Spring Harbor Laboratory, New York. Thus, it is within the skill of those in the genetic engineering art to extract DNA from microbial cells, perform restriction enzyme digestions, electrophorese DNA fragments, tail and anneal plasmid and insert DNA, ligate DNA, transform cells, prepare plasmid DNA, electrophorese proteins, and sequence DNA.

The B.t. cells may be formulated in a variety of ways. They may be employed as wettable powders, granules or dusts, by mixing with various inert materials, such as inorganic minerals (phyllosilicates, carbonates, sulfates, phosphates, and the like) or botanical materials (powdered corncobs, rice hulls, walnut shells, and the like). The formulations may include spreader-sticker adjuvants, stabilizing agents, other pesticidal additives, or surfactants. Liquid formulations may be aqueous-based or non-aqueous and employed as foams, gels, suspensions, emulsifiable concentrates, or the like. The ingredients may include rheological agents, surfactants, emulsifiers, dispersants, or polymers.

The nematicide concentration will vary widely depending upon the nature of the particular formulation, particularly whether it is a concentrate or to be used directly. The nematicide will be present in at least 1% by weight and may be 100% by weight. The dry formulations will have from about 1–95% by weight of the nematicide while the liquid formulations will generally be from about 1–60% by weight of the solids in the liquid phase. The formulations will generally have from about $10^2$ to about $10^4$ cells/mg. These fomulations will be administered at about 50 mg (liquid or dry) to 1 kg or more per hectare.

The formulations can be applied to the environment of the nematodes, e.g., plants, soil or water, by spraying, dusting, sprinkling, or the like.

Following are examples which illustrate procedures, including the best mode, for practicing the invention. These examples should not be construed as limiting. All percentages are by weight and all solvent mixture proportions are by volume unless otherwise noted.

EXAMPLE 1

Culturing B.t. Isolates of the Invention

A subculture of a B.t. isolate can be used to inoculate the following medium, a peptone, glucose, salts medium.

| | |
|---|---|
| Bacto Peptone | 7.5 g/l |
| Glucose | 1.0 g/l |
| $KH_2PO_4$ | 3.4 g/l |
| $K_2HPO_4$ | 4.35 g/l |
| Salts Solution | 5.0 ml/l |
| $CaCl_2$ Solution | 5.0 ml/l |
| Salts Solution (100 ml) | |
| $MgSO_4 \cdot 7H_2O$ | 2.46 g |
| $MnSO_4 \cdot H_2O$ | 0.04 g |
| $ZnSO_4 \cdot 7H_2O$ | 0.28 g |
| $FeSO_4 \cdot 7H_2O$ | 0.40 g |
| $CaCl_2$ Solution (100 ml) | |
| $CaCl_2 \cdot 2H_2O$ | 3.66 g |
| pH 7.2 | |

The salts solution and $CaCl_2$ solution are filter-sterilized and added to the autoclaved and cooked broth at the time of inoculation. Flasks are incubated at 30° C. on a rotary shaker at 200 rpm for 64 hr.

EXAMPLE 2

Purification of Protein and Amino Acid Sequencing

The B.t. isolates PS17, PS63B, PS52A1, and PS69D1 were cultured as described in Example 1. The parasporal inclusion bodies were partially purified by sodium bromide (28–38%) isopycnic gradient centrifugation (Pfannenstiel, M. A., E. J. Ross, V. C. Kramer, and K. W. Nickerson [1984] FEMS Microbiol. Lett. 21:39). The proteins toxic for the nematode *Caenorhabditis elegans* were bound to PVDF membranes (Millipore, Bedford, Mass.) by western blotting techniques (Towbin, H., T. Staehlelin, and K. Gordon [1979] Proc. Natl. Acad. Sci. USA 76:4350) and the N-terminal amino acid sequences were determined by the standard Edman reaction with an automated gas-phase sequenator (Hunkapiller, M. W., R. M. Hewick, W. L. Dreyer, and L. E. Hood [1983] Meth. Enzymol. 91:399). The sequences obtained were:

PS17a: AILNELYPSVPYNV (SEQ ID NO. 17)
PS17b: AILNELYPSVPYNV (SEQ ID NO. 18)
PS52A1: MIIDSKTTLPRHSLINT (SEQ ID NO. 19)
PS63B: QLQAQPLIPYNVLA (SEQ ID NO. 20)

PS69D1: MILGNGKTLPKHIRLAHIFATQNS (SEQ ID NO. 21)

PS33F2: ATLNEVYPVN (SEQ ID NO. 22)

In addition, internal amino acid sequence data were derived for PS63B. The toxin protein was partially digested with Staphylococcus aureus V8 protease (Sigma Chem. Co., St. Louis, Mo.) essentially as described (Cleveland, D. W., S. G. Fischer, M. W. Kirschner, and U. K. Laemmli [1977] J. Biol. Chem. 252:1102). The digested material was blotted onto PVDF membrane and a ca. 28 kDa limit peptide was selected for N-terminal sequencing as described above. The sequence obtained was:

PS63B(2) VQRILDEKLSFQLIK (SEQ ID NO. 23)

From these sequence data oligonucleotide probes were designed by utilizing a codon frequency table assembled from available sequence data of other B.t. toxin genes. The probes were synthesized on an Applied Biosystems, Inc. DNA synthesis machine.

Protein purification and subsequent amino acid analysis of the N-terminal peptides listed above has led to the deduction of several oligonucleotide probes for the isolation of toxin genes from nematicidal B.t. isolates. RFLP analysis of restricted total cellular DNA using radiolabeled oligonucleotide probes has elucidated different genes or gene fragments.

EXAMPLE 3

Cloning of Novel Toxin Genes and Transformation into Escherichia coli

Total cellular DNA was prepared by growing the cells B. t. PS17 to a low optical density ($OD6_{600}$=1.0) and recovering the cells by centrifugation. The cells were protoplasted in TES buffer (30 mM Tris-Cl, 10 mM EDTA, 50 mM NaCl, pH=8.0) containing 20% sucrose and 50 mg/ml lysozyme. The protoplasts were lysed by addition of SDS to a final concentration of 4%. The cellular material was precipitated overnight at 4° C. in 100 mM (final concentration) neutral potassium chloride. The supernate was extracted twice with phenol/chloroform (1:1). The DNA was precipitated with ethanol and purified by isopycnic banding on a cesium chloride-ethidium bromide gradient.

Total cellular DNA from PS17 was digested with EcoRI and separated by electrophoresis on a 0.8% (w/v) Agarose-TAE (50 mM Tris-HCl, 20 mM NaOAc, 2.5 mM EDTA, pH=8.0) buffered gel. A Southern blot of the gel was hybridized with a [$^{32}$p]-radiolabeled oligonucleotide probe derived from the N-termninal amino acid sequence of purified 130 kDa protein from PS17. The sequence of the oligonucleotide synthesized is (GCAATTTTAAATGAATTATATCC) (SEQ ID NO. 24). Results showed that the hybridizing EcoRI fragments of PS17 are 5.0 kb, 4.5 kb, 2.7 kb and 1.8 kb in size, presumptively identifying at least four new nematode-active toxin genes, PS17 d, PS17b, PS17a and PS17e, respectively.

A library was constructed from PS17 total cellular DNA partially digested with Sau3A and size fractionated by electrophoresis. The 9 to 23 kb region of the gel was excised and the DNA was electroeluted and then concentrated using an Elutip™ ion exchange column (Schleicher and Schuel, Keene N.H.). The isolated Sau3A fragments were ligated into LambdaGEM-11™ (PROMEGA). The packaged phage were plated on KW251 E. coli cells (PROMEGA) at a high titer and screened using the above radiolabeled synthetic oligonucleotide as a nucleic acid hybridization probe. Hybridizing plaques were purified and rescreened at a lower plaque density. Single isolated purified plaques that hybridized with the probe were used to infect KW251 E. coli cells in liquid culture for preparation of phage for DNA isolation. DNA was isolated by standard procedures.

Recovered recombinant phage DNA was digested with EcoRi and separated by electrophoresis on a 0.8% agarose-TAE gel. The gel was Southern blotted and hybridized with the oligonucleotide probe to characterize the toxin genes isolated from the lambda library. Two patterns were present, clones containing the 4.5 kb (PS17b) or the 2.7 kb (PS 17a) EcoRI fragments. Preparative amounts of phage DNA were digested with SalI (to release the inserted DNA from lambda arms) and separated by electrophoresis on a 0.6% agarose-TAE gel. The large fragments, electroeluted and concentrated as described above, were ligated to SalI-digested and dephosphorylated pBClac, an E. coliIB.t. shuttle vector comprised of replication origins from pBC16 and pUC19. The ligation mix was introduced by transformation into NM522 competent E. coli cells and plated on LB agar containing ampicillin, isopropyl-(Beta)-D-thiogalactoside (IPTG) and 5-Bromo-4-Chloro-3-indolyl-(Beta)-D-galactoside (XGAL). White colonies, with putative insertions in the (Beta)--galactosidase gene of pBClac, were subjected to standard rapid plasmid purification procedures to isolate the desired plasmids. The selected plasmid containing the 2.7 kb EcoRI fragment was named pMYC1627 and the plasmid containing the 4.5 kb EcoRI fragment was called pMYC1628.

The toxin genes were sequenced by the standard Sanger dideoxy chain termination method using the synthetic oligonucleotide probe, disclosed above, and by "walking" with primers made to the sequence of the new toxin genes.

The PS17 toxin genes were subcloned into the shuttle vector pHT3101 (Lereclus, D. et al. [1989] FEMS Microbiol. Lett. 60:211–218) using standard methods for expression in B.t. Briefly, SalI fragments containing the 17a and 17b toxin genes were isolated from pMYC1629 and pMYC1627, respectively, by preparative agarose gel electrophoresis, electroelution, and concentrated, as described above. These concentrated fragments were ligated into SalI-cleaved and dephosphorylated pHT3101. The ligation mixtures were used separately to transform frozen, competent E. coli NM522. Plasmids from each respective recombinant E. coli strain were prepared by alkaline lysis and analyzed by agarose gel electrophoresis. The resulting subclones, pMYC2311 and pMYC2309, harbored the 17a and 17b toxin genes, respectively. These plasmids were transformed into the acrystalliferous B.t. strain, HD-1 cryB (Aronson, A., Purdue University, West Lafayette, Ind.), by standard electroporation techniques (Instruction Manual, Biorad, Richmond, Calif.).

Recombinant B.t. strains HD-1 cryB [pMYC2311] and [pMYC2309] were grown to sporulation and the proteins purified by NaBr gradient centrifugation as described above for the wild-type B.t. proteins.

EXAMPLE 4

Activity of the B.t. Toxin Protein and Gene Product Against Caenorhabditis elegans Caenorhabditis elegans (CE) was cultured as described by Simpkin and Coles (J. Chem. Tech. Biotechnol. 31:66–69, 1981) in coming (Coming Glass Works, Corning, N.Y.) 24-well tissue culture plates containing 1 ml S-basal media, 0.5 mg ampicillin and 0.01 mg cholesterol. Each well also contained ca. $10^8$ cells of Escherichia coli strain OP-50, a uracil auxotroph. The wells were seeded with ca. 100–200 CE per well and incubated at 20° C. Samples of protein (obtained from the wild type B.t. or the recombinant B.t.) were added to the wells by serial dilution. Water served as the control as well as the vehicle to introduce the proteins to the wells.

Each of the wells were examined daily and representative results are as follows:

| µg Toxin | % Kill with protein from indicated isolate | | |
| --- | --- | --- | --- |
| | HD-1 cryB [pMYC2309] | HD-1 cryB [MYC2311] | PS17 |
| 100 | 25 | 50 | 75 |
| 32 | 25 | 50 | 75 |
| 10 | 50 | 25 | 50 |
| 1 | 0 | 0 | 0 |

EXAMPLE 5

Molecular Cloning of Gene Encoding a Novel Toxin From *Bacillus thuringiensis* Strain PS52A1

Total cellular DNA was prepared from *Bacillus thuringiensis* PS52A1 (*B.t.* PS52A1) as disclosed in Example 3.

RFLP analyses were performed by standard hybridization of Southern blots of PS52A1 DNA with a $^{32}$P-labeled oligonucleotide probe designed from the N-terminal amino acid sequence disclosed in Example 2. The sequence of this probe is:

5' ATG ATT ATT GAT TCT AAA ACA ACA TTA CCA AGA CAT TCA/T TTA ATA/T AAT ACA/T ATA/T AA 3' (SEQ ID NO. 25)

This probe was designated 52A1-C. Hybridizing bands included an approximately 3.6 kbp HindIII fragment and an approximately 8.6 kbp EcoRV fragment. A gene library was constructed from PS52A1 DNA partially digested with Sau3A. Partial restriction digests were fractionated by agarose gel electrophoresis. DNA fragments 6.6 to 23 kbp in size were excised from the gel, electroeluted from the gel slice, and recovered by ethanol precipitation after purification on an Elutip-D ion exchange column. The Sau3A inserts were ligated into BamHI-digested LambdaGem- 11 (Promega). Recombinant phage were packaged and plated on *E. coli* KW251 cells (Promega). Plaques were screened by hybridization with the radiolabeled 52A1-C oligonucleotide probe disclosed above. Hybridizing phage were plaque-purified and used to infect liquid cultures of *E. coli* KW251 cells for isolation of phage DNA by standard procedures (Maniatis et al.). For subcloning, preparative amounts of DNA were digested with EcoRI and SalI, and electrophoresed on an agarose gel. The approximately 3.1 kbp band containing the toxin gene was excised from the gel, electroeluted from the gel slice, and purified by ion exchange chromatography as above. The purified DNA insert was ligated into EcoRI+SalI-digested pHTBlueII (an *E. coli/B. thuringiensis* shuttle vector comprised of pBluescript S/K [Stratagene] and the replication origin from a resident *B.t.* plasmid [D. Lereclus et al. 1989. FEMS Microbiology Letters 60:211–218]). The ligation mix was used to transform frozen, competent *E. coli* NM522 cells (ATCC 47000). Transformants were plated on LB agar containing ampicillin, isopropyl-(Beta)-D-thiogalactoside (IPTG), and 5-Bromo-4-Chloro-3-indolyl-(Beta)-D-galactoside (XGAL). Plasmids were purified from putative recombinants by alkaline lysis (Maniatis et al.) and analyzed by electrophoresis of EcoRI and SalI digests on agarose gels. The desired plasmid construct, pMYC2321 contains a toxin gene that is novel compared to the maps of other toxin genes encoding nematicidal proteins.

Plasmid pMYC2321 was introduced into an acrystalliferous (Cry$^-$) *B.t.* host by electroporation. Expression of an approximately 55–60 kDa crystal protein was verified by SDS-PAGE analysis. NaBr-purified crystals were prepared as described in Example 3 for determination of toxicity of the cloned gene product to Pratylenchus spp.

EXAMPLE 6

Activity of the *B.t.* PS52A1 Toxin Protein and Gene Product Against the Root Lesion Nematode *Pratylenchus Scribneri*

*Pratylenchus scribneri* was reared aseptically on excised corn roots in Gamborg's B5 medium (GIBCO Laboratories, Grand Island, N.Y.). Bioassays were done in 24 well assay plates (Corning #25820) using L 3–4 larvae as described by Tsai and Van Gundy (J. Nematol. 22(3):327–332). Approximately 20 nematodes were placed in each well. A total of 80–160 nematodes were used in each treatment. Samples of protein were suspended in aqueous solution using a hand-held homogenizer.

Mortality was assessed by prodding with a dull probe 7 days after treatment. Larvae that did not respond to prodding were considered moribund. Representative results are shown below.

| Rate (ppm) | Percent Moribund |
| --- | --- |
| 200 | 75 |
| Control | 5 |

EXAMPLE 7

Molecular Cloning of Gene Encoding a Novel Toxin From *Bacillus Thuringiensis* Strain PS69D1

Total cellular DNA was prepared from PS69D1 (*B.t.* PS69D1) as disclosed in Example 3. RFLP analyses were performed by standard hybridization of Southern blots of PS69D1 DNA with a 32P-labeled oligonucleotide probe designated as 69D1-D. The sequence of the 69D1-D probe was:

5' AAA CAT ATT AGA TTA GCA CAT ATT TTT GCA ACA CAA AA 3' (SEQ ID NO. 26)

Hybridizing bands included an approximately 2.0 kbp HindIII fragment.

A gene library was constructed from PS69D1 DNA partially digested with Sau3A. Partial restriction digests were fractionated by agarose gel electrophoresis. DNA fragments 6.6 to 23 kbp in size were excised from the gel, electroeluted from the gel slice, and recovered by ethanol precipitation after purification on an Elutip-D ion exchange column. The Sau3A inserts were ligated into BamHI-digested LambdaGem-11 (Promega, Madison, Wis.). Recombinant phage were packaged and plated on *E. coli* KW251 cells (Promega, Madison, Wis.). Plaques were screened by hybridization with the radiolabeled 69D1-D oligonucleotide probe. Hybridizing phage were plaque-purified and used to infect liquid cultures of *E. coli* KW251 cells for isolation of phage DNA by standard procedures (Maniatis et al. [1982]

*Molecular Cloning: A Laboratory Manual*, Cold Spring Harbor, N.Y.). For subcloning, preparative amounts of DNA were digested with HindIII and electrophoresed on an agarose gel. The approximately, 2.0 kbp band containing the toxin gene was excised from the gel, electroeluted from the gel slice, and purified by ion exchange chromatography as above. The purified DNA insert was ligated into HindIII-digested pHTBlueII (and *E. coli/B.t.* shuttle vector comprised of pBluescript S/K (Stratagene, San Diego, Calif.) and the replication origin from a resident *B.t.* plasmid (D. Lereclus et al [1989] FEMS Microbiol. Lett. 60:211–218). The ligation mix was used to transform frozen, competent *E. coli* NM522 cells (ATCC 47000). Transformants were plated on LB agar containing 5-bromo-4-chloro-3-indolyl-(Beta)-D-galactoside (XGAL). Plasmids were purified from putative recombinants by alkaline lysis (Maniatis et al., supra) and analyzed by electrophoresis of HindIII digests on agarose gels. The desired plasmid construct, pMYC2317, contains a toxin gene that is novel compared to the maps of other toxin genes encoding insecticidal proteins.

EXAMPLE 8

Molecular Cloning of a Gene Encoding a Novel Toxin from *Bacillus thuringiensis* Strain PS63B Example 2 shows the aminoterminal and internal polypeptide sequences of the PS63B toxin protein as determined by standard Edman protein sequencing. From these sequences, two oligonucleotide primers were designed using a codon frequency table assembled from *B.t.* genes encoding δ-endotoxins. The sequence of the forward primer (63B-A) was complementary to the predicted DNA sequence at the 5' end of the gene:

63B-A - 5' CAA T/CTA CAA GCA/T CAA CC 3' (SEQ ID NO. 27)

The sequence of the reverse primer (63B-INT) was complementary to the inverse of the internal predicted DNA sequence:

63B-INT - 5' TTC ATC TAA AAT TCT TTG A/TAC 3' (SEQ ID NO. 28)

These primers were used in standard polymerase chain reactions (Cetus Corporation) to amplify an approximately 460 bp fragment of the 63B toxin gene for use as a DNA cloning probe. Standard Southern blots of total cellular DNA from PS63B were hybridized with the radiolabeled PCR probe. Hybridizing bands included an approximately 4.4 kbp XbaI fragment, an approximately 2.0 kbp HindIII fragment, and an approximately 6.4 kbp SpeI fragment.

Total cellular DNA was prepared from *Bacillus thuringiensis* (*B.t.*) cells grown to an optical density of 1.0 at 600 nm. The cells were recovered by centrifugation and protoplasts were prepared in lysis mix (300 mM sucrose, 25 mM Tris-HCl, 25 mM EDTA, pH=8.0) and lysozyme at a concentration of 20 mg/ml. The protoplasts were ruptured by addition of ten volumes of 0.1 M NaCl, 0.1 M Tris-HCl pH 8.0, and 0.1% SDS. The cellular material was quickly frozen at −70° C. and thawed to 37° C. twice. The supernatant was extracted twice with phenol/chloroform (1:1). The nucleic acids were precipitated with ethanol. To remove as much RNA as possible from the DNA preparation, RNase at final concentration of 200 μg/ml was added. After incubation at 37° C. for 1 hour, the solution was extracted once with phenol/chloroform and precipitated with ethanol.

A gene library was constructed from PS63B total cellular DNA partially digested with NdeII and size fractioned by gel electrophoresis. The 9–23 kb region of the gel was excised and the DNA was electroeluted and then concentrated using an Elutip-d ion exchange column (Schleicher and Schuel, Keene, N.H.). The isolated NdeII fragments were ligated into BamHI-digested LambdaGEM-11 (PROMEGA). The packaged phage were plated on *E. coli* KW251 cells (PROMEGA) at a high titer and screened using the radiolabeled approximately 430 bp fragment probe amplified with the 63B-A and 63B internal primers (SEQ ID NOS. 27 and 28, respectively) by polymerase chain reaction. Hybridizing plaques were purified and rescreened at a lower plaque density. Single isolated, purified plaques that hybridized with the probe were used to infect KW251 cells in liquid culture for preparation of phage for DNA isolation. DNA was isolated by standard procedures (Maniatis et al., supra). Preparative amounts of DNA were digested with SalI (to release the inserted DNA from lambda sequences) and separated by electrophoresis on a 0.6% agarose-TAE gel. The large fragments were purified by ion exchange chromatography as above and ligated to SalI-digested, dephosphorylated pHTBlueII (an *E. coli/B. t.* shuttle vector comprised of pBlueScript S/K [Stratagene, San Diego, Calif.] and the replication origin from a resident *B.t.* plasmid [Lereclus, D. et al. (1989) FEMS Microbiol. Lett. 60:211–218]). The ligation mix was introduced by transformation into competent *E. coli* NM522 cells (ATCC 47000) and plated on LB agar containing ampicillin (100 μg/ml), IPTG (2%), and XGAL (2%). White colonies, with putative restriction fragment insertions in the (Beta)-galactosidase gene of pHTBlueII, were subjected to standard rapid plasmid purification procedures (Maniatis et al., supra). Plasmids ere analyzed by SalI digestion and agarose gel electrophoresis. The desired plasmid construct, pMYC1641, contains an approximately 14 kb SalI insert.

For subcloning, preparative amounts of DNA were digested with XbaI and electrophoresed on an agarose gel. The approximately 4.4 kbp band containing the toxin gene was excised from the gel, electroeluted from the gel slice, and purified by ion exchange chromatography as above. This fragment was ligated into XbaI cut pHTBlueII and the resultant plasmid was designated pMYC1642.

EXAMPLE 9

Cloning of a Novel Toxin Gene From *B.t.* PS33F2 and Transformation into *Escherichia coli*

Total cellular DNA was prepared from *B.t.* PS33F2 cells grown to an optical density, at 600 nm, of 1.0. Cells were pelleted by centrifugation and resuspended in protoplast buffer (20 mg/ml lysozyme in 0.3 M sucrose, 25 mM Tris-Cl [pH 8.0], 25 mM EDTA). After incubation at 37° C. for 1 hour, protoplasts were lysed by the addition of nine volumes of a solution of 0.1 M NaCl, 0.1% SDS, 0.1 M Tris-Cl followed by two cycles of freezing and thawing. The cleared lysate was extracted twice with phenol:chloroform (1:1). Nucleic acids were precipitated with two volumes of ethanol and pelleted by centrifugation. The pellet was resuspended in 10 mM Tris-Cl, 1 mM EDTA (TE) and RNase was added to a final concentration of 50 μg/ml. After incubation at 37° C. for 1 hour, the solution was extracted once each with phenol:chloroform (1:1) and TE-saturated chloroform. DNA was precipitated from the aqueous phase by the addition of one-tenth volume of 3 M NaOAc and two volumes of ethanol. DNA was pelleted by centrifugation, washed with 70% ethanol, dried, and resuspended in TE.

Plasmid DNA was extracted from protoplasts prepared as described above. Protoplasts were lysed by the addition of nine volumes of a solution of 10 mM Tris-Cl, 1 mM EDTA, 0.085 NNaOH, 0.1% SDS, pH=8.0. SDS was added to 1% final concentration to complete lysis. One-half volume of 3 M KOAc was then added and the cellular material was precipitated overnight at 4° C. After centrifugation, the DNA was precipitated with ethanol and plasmids were purified by isopycnic centrifugation on cesium chloride-ethidium bromide gradients.

Restriction Fragment Length Polymorphism (RFLP) analyses were performed by standard hybridization of Southern blots of PS33F2 plasmid and total cellular DNA with $^{32}$P-labelled oligonucleotide probes designed to the N-terminal amino acid sequence disclosed in Example 2.

Probe 33F2A: 5' GCA/T ACA/T TTA AAT GAA GTA/T TAT 3' (SEQ ID NO. 33)

Probe 33F2B: 5' AAT GAA GTA/T TAT CCA/T GTA/T AAT 3' (SEQ ID NO. 34)

Hybridizing bands included an approximately 5.85 kbp EcoRI fragment. Probe 33F2A and a reverse PCR primer were used to amplify a DNA fragment of approximately 1.8 kbp for use as a hybridization probe for cloning the PS33F2 toxin gene. The sequence of the reverse primer was:

5' GCAAGCGGCCGCTTATGGAATAAATTCAATT C/T T/G A/G TC T/A A 3' (SEQ ID NO. 35).

A gene library was constructed from PS33F2 plasmid DNA digested with EcoRI. Restriction digests were fractionated by agarose gel electrophoresis. DNA fragments 4.3–6.6 kbp were excised from the gel, electroeluted from the gel slice, and recovered by ethanol precipitation after purification on an Elutip-D ion exchange column (Schleicher and Schuel, Keene N.H.). The EcoRI inserts were ligated into EcoRI-digested pHTBlueII (an *E. coli/B. thuringiensis* shuttle vector comprised of pBluescript S/K [Stratagene] and the replication origin from a resident*B.t.* plasmid [D. Lereclus et al. 1989. FEMS Microbial. Lett. 60:211–218]). The ligation mixture was transformed into frozen, competent NM522 cells (ATCC 47000). Transformants were plated on LB agar containing ampicillin, isopropyl -(Beta)-D-thiogalactoside (IPTG), and 5-bromo-4-chloro-3-indolyl-(Beta)-D-galactoside (XGAL). Colonies were screened by hybridization with the radiolabeled PCR amplified probe described above. Plasmids were purified from putative toxin gene clones by alkaline lysis and analyzed by agarose gel electrophoresis of restriction digests. The desired plasmid construct, pMYC2316, contains an approximately 5.85 kbp Eco4RI insert; the toxin gene residing on this DNA fragment (33F2a) is novel compared to the DNA sequences of other toxin genes encoding nematicidal proteins.

Plasmid pWYC2316 was introduced into the acrystalliferous (Cry-) *B.t.* host, HD-1 CryB (A. Aronson, Purdue University, West Lafayette, Ind.) by electrdporation. Expression of an approximately 120–140 kDa crystal protein was verified by SDS-PAGE analysis.

Crystals were purified on NaBr gradients (M. A. Pfannenstiel et al. 1984. FEMS Microbiol. Lett. 21:39) for determination of toxicity of the cloned gene product to Pratylenchus spp.

EXAMPLE 10

Activity of the *B.t.* Gene Product 33F2 Against the Plant Nematode Pratylenchus Spp.

Pratylenchus spp. was reared aseptically on excised corn roots in Gamborg's B5 medium (GIBCO® Laboratories, Grand Island, N.Y.) Bioassays were done in 24 well assay plates (Corning #25820) using L 3–4 larvae as described by Tsai and van Gundy (J. Nematol. 22(3):327–332). Approximately 20 nematodes were placed in each well. A total of 80–160 nematodes were used in each treatment. Samples of protein were suspended in an aqueous solution using a hand-held Dounce homogenizer.

Mortality was assessed visually 3 days after treatment. Larvae that were nearly straight and not moving were considered moribund. Representative results are as follows:

| 33F2a (ppm) | % Moribund |
|---|---|
| 0 | 12 |
| 75 | 78 |

Species of Pratylenchus, for example *P. scribneri*, are known pathogens of many economically important crops including corn, peanuts, soybean, alfalfa, beans, tomato, and citrus. These "root lesion" nematodes are the second most economically damaging genus of plant parasitic nematodes (after Meloidogyne-the "root knot" nematode), and typify the migratory endoparasites.

EXAMPLE 11

Cloning of Novel Nematode-Active Genes Usino Generic Oligonucleotide Primers The nematicidal gene of a new nematicidal *B.t.* can be obtained from DNA of the strain by performing the standard polymerase chain reaction procedure as in Example 8 using the oligonucleotides of SEQ ID NO. 32 or SEQ ID NO. 30 as reverse primers and SEQ ID NO. 14, SEQ ID NO. 16, SEQ ID NO. 24, Probe B of SEQ ID NO. 5 (AAT GAA GTA/T TAT CCA/T GTA/T AAT), or SEQ ID NO. 27 as forward primers. The expected PCR fragments would be approximately 330 to 600 bp (with either reverse primer and SEQ ID NO. 14), 1000 to 1400 bp (with either reverse primer and SEQ ID NO. 16), and 1800 to 2100 bp (with either reverse primer and any of the three N-terminal primers, SEQ ID NO. 5 (Probe B), SEQ ID NO. 24, and SEQ ID NO. 27). Alternatively, a complement from the primer family described by SEQ ID NO. 14 can be used as reverse primer with SEQ ID NO. 16, SEQ ID NO. 24, SEQ ID NO. 5 (Probe B), or SEQ ID NO. 27 as forward primers. The expected PCR fragments would be approximately 650 to 1000 bp with SEQ ID NO. 16, and 1400 to 1800 bp (for the three N-terminal primers, SEQ ID NO. 5 (Probe B), SEQ ID NO. 24, and SEQ ID NO. 27). Amplified DNA fragments of the indicated sizes can be radiolabeled and used as probes to clone the entire gene as in Example 8.

EXAMPLE 12

Further Cloning of Novel Nematode-Active Genes Using Generic Oligonucleotide Primers A gene coding for a nematicidal toxin a new nematicidal *B.t.* isolate can also be obtained from DNA of the strain by performing the standard polymerase chain reaction procedure as in Example 8 using oligonucleotides derived from the PS52A1 and PS69D1 gene sequences as follows:

1. Forward primer "TGATTTT(T or A)(C or A)TCAATTATAT(A or G)A(G or T)GTTTAT" (SEQ ID NO. 36) can be used with primers complementary to probe "AAGAGTTA(C or T)TA(A or G)A(G or A)AAAGTA" (SEQ ID NO. 37), probe "TTAGGACCATT(A or G)(C or T)T(T or A)GGATTTGTTGT(A or T)TATGAAAT" (SEQ ID NO. 38), and probe "GA(C or T)AGAGATGT(A or T)AAAAT(C or T)(T or A)TAGGAATG" (SEQ ID NO. 39) to produce amplified fragments of approximately 440, 540, and 650 bp, respectively.

2. Forward primer "TT(A or C)TTAAA(A or T)C(A or T)GCTAATGATATT" (SEQ ID NO. 40) can be used with primers complementary to SEQ ID NO. 37, SEQ ID NO. 38, and SEQ ID NO. 39 to produce amplified fragments of approximately 360,460, and 570 bp, respectively.

3. Forward primer SEQ ID NO. 37 can be used with primers complementary to SEQ ID NO. 38 and SEQ ID NO. 39 to produce amplified fragments of approximately 100 and 215 bp, respectively.

Amplified DNA fragments of the indicated sizes can be radiolabeled and used as probes to clone the entire gene as in Example 8.

EXAMPLE 13

Insertion of Toxin Gene Into Plants

One aspect of the subject invention is the transformation of plants with genes coding for a nematicidal toxin. The transformed plants are resistant to attack by nematodes.

Genes coding for nematicidal toxins, as disclosed herein, can be inserted into plant cells using a variety of techniques which are well known in the art. For example, a large number of cloning vectors comprising a replication system in E. coli and a marker that permits selection of the transformed cells are available for preparation for the insertion of foreign genes into higher plants. The vectors comprise, for example, pBR322, pUC series, M13 mp series, pACYC184, etc. Accordingly, the sequence coding for the B.t. toxin can be inserted into the vector at a suitable restriction site. The resulting plasmid is used for transformation into E. coli. The E. coli cells are cultivated in a suitable nutrient medium, then harvested and lysed. The plasmid is recovered. Sequence analysis, restriction analysis, electrophoresis, and other biochemical-molecular biological methods are generally carried out as methods of analysis. After each manipulation, the DNA sequence used can be cleaved and joined to the next DNA sequence. Each plasmid sequence can be cloned in the same or other plasmids. Depending on the method of inserting desired genes into the plant, other DNA sequences may be necessary. If, for example, the Ti or Ri plasmid is used for the transformation of the plant cell, then at least the right border, but often the right and the left border of the Ti or Ri plasmid T-DNA, has to be joined as the flanking region of the genes to be inserted.

The use of T-DNA for the transformation of plant cells has been intensively researched and sufficiently described in EP 120 516; Hoekema (1985) In: *The Binary Plant Vector System*, Offset-durkkerij Kanters B.V., Alblasserdam, Chapter 5; Fraley et al., Crit. Rev. Plant Sci. 4:1–46; and An et al. (1985) EMBO J. 4:277–287.

Once the inserted DNA has been integrated in the genome, it is relatively stable there and, as a rule, does not come out again. It normally contains a selection marker that confers on the transformed plant cells resistance to a biocide or an antibiotic, such as kanamycin, G 418, bleomycin, hygromycin, or chloramphenicol, inter alia. The individually employed marker should accordingly permit the selection of transformed cells rather than cells that do not contain the inserted DNA.

A large number of techniques are available for inserting DNA into a plant host cell. Those techniques include transformation with T-DNA using *Agrobacterium tumefaciens* or *Agrobacterium rhizogenes* as transformation agent, fusion, injection, or electroporation as well as other possible methods. If agrobacteria are used for the transformation, the DNA to be inserted has to be cloned into special plasmids, namely either into an intermediate vector or into a binary vector. The intermediate vectors can be integrated into the Ti or Ri plasmid by homologous recombination owing to sequences that are homologous to sequences in the T-DNA. The Ti or Ri plasmid also comprises the air region necessary for the transfer of the T-DNA. Intermediate vectors cannot replicate themselves in agrobacteria. The intermediate vector can be transferred into *Agrobacterium tumefaciens* by means of a helper plasmid (conjugation). Binary vectors can replicate themselves both in *E. coli* and in agrobacteria. They comprise a selection marker gene and a linker or polylinker which are framed by the right and left T-DNA border regions. They can be transformed directly into agrobacteria (Holsters et al. [1978] Mol. Gen. Genet. 163:181–187). The agrobacterium used as host cell is to comprise a plasmid carrying a air region. The air region is necessary for the transfer of the T-DNA into the plant cell. Additional T-DNA may be contained. The bacterium so transformed is used for the transformation of plant cells. Plant explants can advantageously be cultivated with *Agrobacterium tumefaciens* or *Agrobacterium rhizogenes* for the transfer of the DNA into the plant cell. Whole plants can then be regenerated from the infected plant material (for example, pieces of leaf, segments of stalk, roots, but also protoplasts or suspension-cultivated cells) in a suitable medium, which may contain antibiotics or biocides for selection. The plants so obtained can then be tested for the presence of the inserted DNA. No special demands are made of the plasmids in the case of injection and electroporation. It is possible to use ordinary plasmids, such as, for example, pUC derivatives.

The transformed cells grow inside the plants in the usual manner. They can form germ cells and transmit the transformed trait(s) to progeny plants. Such plants can be grown in the normal manner and crossed with plants that have the same transformed hereditary factors or other hereditary factors. The resulting hybrid individuals have the corresponding phenotypic properties.

It should be understood that the examples and embodiments described herein are for illustrative purposes only and that various modifications or changes in light thereof will be suggested to persons skilled in the art and are to be included within the spirit and purview of this application and the scope of the appended claims.

What is claimed is:

1. An isolated oligonucleotide consisting of a nuclcotide Sequence that encodes SEQ ID NO:31.

2. An isolated oligonucleotide consisting essentially of a nuclcotide sequence that encodes an amino acid sequence selected from the group consisting SEQ ID NO:13, SEQ ID NO:15, and SEQ ID NO:29.

3. The oligonucleotide of claim 2 wherein said amino acid sequence is SEQ ID NO:13.

4. The oligonucleotide of claim 2 wherein said amino acid sequence is SEQ ID NO:15.

5. The oligonucleotide of claim 2 wherein said amino acid sequence is SEQ ID NO:29.

6. An isolated oligonuclotide consisting essentially of nucleotide sequence selected from the group consisting of SEQ ID NO:14, SEQ ID NO:16, SEQ ID NO:30, SEQ ID NO:32, SEQ ID NO:35, SEQ ID NO:36, SEQ ID NO:37, SEQ ID NO:38, SEQ ID NO: 39, SEQ ID NO:40.

7. The oligonucleotide according to claim 6 wherein said nucleotide sequence is SQE ID NO:14.

8. The oligonucleotide according to claim 6 wherein said nucloeotide sequence is SEQ ID NO:16.

9. The oligonucleotide according to claim 6 wherein said nucleotide sequence is SEQ ID NO:30.

10. The oligonucleotide according to claim 6 wherein said nucleotide sequence is SEQ ID NO:32.

11. The oligonucleotide according to claim 6 wherein said nucleotide sequence is SEQ ID NO:35.

12. The oligonucleotide according to claim 6 wherein said nucleotide sequence is SEQ ID NO:36.

13. The oligonucleotide according to claim 6 wherein said nucleotide sequence is SEQ ID NO:37.

14. The oligonucleotide according to claim 6 wherein said nucleotide sequence is SEQ ID NO:38.

15. The oligonucleotide according to claim 6 wherein said nucleotide sequence is SEQ ID NO:39.

16. The oligonucleotide according to claim 6 wherein said nucleotide sequence is SEQ ID NO:40.

* * * * *

UNITED STATES PATENT AND TRADEMARK OFFICE
CERTIFICATE OF CORRECTION

PATENT NO. : 6,166,195
DATED : December 20, 2000
INVENTOR(S) : Schnepf et al.

It is certified that error appears in the above-identified patent and that said Letters Patent is hereby corrected as shown below:

Column 4,
Line 41, "OXXXBXXXEUXBKXBJJXX" should read
-- OXxXXBXXXE UXBKXBJJXX --
Line 42, "XXVUXXZLZLB" should read -- XXVUXZLZLB --.
Line 53, "*LEE" should read -- *LE --.
Line 67, "ZXUPLXXUYBX" should read -- ZXUPLXXUBX --.

Column 5,
Line 38, "ΦXWWU" should read -- 101XWWU --.
Lines 4-5, "XLUZYXXxx" should read -- XLUZYXXxxx --.

Column 8,
Line 15, "Alf" should read -- All --.
Line 36, "35S," should read -- $^{35}$S, --.

Column 10,
Line 39, "Wor Y" should read -- W or Y --.

Column 12,
Line 19, "Helicotylenchius" should read -- Helicotylenchus --.

Column 14,
Line 62, "Pseudomonasfluorescens" should read -- Pseudomonas fluorescens --.

Column 15,
Line 42, "plasrnids" should read -- plasmids --.

Column 17,
Line 32, "(OD6600" should read -- (OD$_{600}$ --.
Line 39, "supemate" should read -- supernate --.
Line 47, "[$^{33}$p-" should read -- [$^{32}$P- --.
Line 55, "PS17 d," should read -- PS17d, --.

Column 18,
Line 6, "EcoRi" should read -- *Eco*RI --.
Line 10, "(PS 17a)" should read -- (PS17a) --.
Line 16, "E. coliIB.t." should read -- *E. coli/B.t.* --.
Line 64, "coming (Coming" should read -- corning (Corning --.

UNITED STATES PATENT AND TRADEMARK OFFICE
CERTIFICATE OF CORRECTION

PATENT NO. : 6,166,195
DATED : December 20, 2000
INVENTOR(S) : Schnepf et al.

It is certified that error appears in the above-identified patent and that said Letters Patent is hereby corrected as shown below:

Column 19,
Line 14, "[MYC2311]" should read -- [pMYC2311] --.

Column 23,
Line 47, "pWYC2316" should read -- pMYC2316 --.
Line 49, "electrdporation" should read -- electroporation --.

Column 24,
Line 24, "Usino" should read -- Using --.

Column 26,
Line 17, "air region" should read -- vir region --.
Line 28, "a air region. The air region" should read -- a vir region. The vir region --.

Column 85, claim 1,
Line 1, "nuclcotide" should read -- nucleotide --.

Column 85, claim 2,
Line 1, "nucleotide" should read -- nucleotide --.

Column 85, claim 6,
Lines 1-2, "of nuclcotide" should read -- of a nucleotide --.
Line 5, "39, SEQ" should read -- 39, and SEQ --.

Column 85, claim 7,
Line 2, "SQE" should read -- SEQ --.

UNITED STATES PATENT AND TRADEMARK OFFICE
CERTIFICATE OF CORRECTION

PATENT NO. : 6,166,195
DATED : December 20, 2000
INVENTOR(S) : Schnepf et al.

It is certified that error appears in the above-identified patent and that said Letters Patent is hereby corrected as shown below:

Column 86, claim 8,
Line 2, "nucloeotide" should read -- nucleotide --.

Signed and Sealed this

Twenty-fifth Day of December, 2001

Attest:

Attesting Officer

JAMES E. ROGAN
Director of the United States Patent and Trademark Office

SEQUENCE LISTING

<160> NUMBER OF SEQ ID NOS: 42

<210> SEQ ID NO 1
<211> LENGTH: 4155
<212> TYPE: DNA
<213> ORGANISM: Bacillus thuringiensis

<400> SEQUENCE: 1

-continued

| | |
|---|---|
| atggcaattt taaatgaatt atatccatct gtaccttata atgtattggc gtatacgcca | 60 |
| ccctcttttt tacctgatgc gggtacacaa gctacacctg ctgacttaac agcttatgaa | 120 |
| caattgttga aaaatttaga aaagggata aatgctggaa cttattcgaa agcaatagct | 180 |
| gatgtactta aaggtatttt tatagatgat acaataaatt atcaaacata tgtaaatatt | 240 |
| ggtttaagtt taattacatt agctgtaccg gaaattggta ttttttacacc tttcatcggt | 300 |
| ttgtttttg ctgcattgaa taaacatgat gctccacctc ctcctaatgc aaaagatata | 360 |
| tttgaggcta tgaaaccagc gattcaagag atgattgata gaactttaac tgcggatgag | 420 |
| caaacattt taaatgggga aataagtggt ttacaaaatt tagcagcaag ataccagtct | 480 |
| acaatggatg atattcaaag ccatggagga tttaataagg tagattctgg attaattaaa | 540 |
| aagtttacag atgaggtact atctttaaat agttttata cagatcgttt acctgtattt | 600 |
| attacagata atacagcgga tcgaactttg ttaggtcttc cttattatgc tatacttgcg | 660 |
| agcatgcatc ttatgttatt aagagatatc attactaagg gtccgacatg ggattctaaa | 720 |
| attaattca caccagatgc aattgattcc tttaaaaccg atattaaaa taatataaag | 780 |
| ctttactcta aaactattta tgacgtattt cagaagggac ttgcttcata cggaacgcct | 840 |
| tctgatttag agtcctttgc aaaaaaacaa aaatatattg aaattatgac aacacattgt | 900 |
| ttagattttg caagattgtt tcctactttt gatccagatc tttatccaac aggatcaggt | 960 |
| gatataagtt tacaaaaaac acgtagaatt ctttctcctt ttatccctat acgtactgca | 1020 |
| gatgggttaa cattaaataa tacttcaatt gatacttcaa attggcctaa ttatgaaaat | 1080 |
| gggaatggcg cgtttccaaa cccaaaagaa agaatattaa aacaattcaa actgtatcct | 1140 |
| agttggagag cgggacagta cggtgggctt ttacaacctt atttatgggc aatagaagtc | 1200 |
| caagattctg tagagactcg tttgtatggg cagcttccag ctgtagatcc acaggcaggg | 1260 |
| cctaattatg tttccataga ttcttctaat ccaatcatac aaataaatat ggatacttgg | 1320 |
| aaaacaccac cacaaggtgc gagtgggtgg aatacaaatt taatgagagg aagtgtaagc | 1380 |
| gggttaagtt tttacaacg agatggtacg agacttagtg ctggtatggg tggtggtttt | 1440 |
| gctgatacaa tatatagtct ccctgcaact cattatcttt cttatctcta tggaactcct | 1500 |
| tatcaaactt ctgataacta ttctggtcac gttggtgcat tggtaggtgt gagtacgcct | 1560 |
| caagaggcta ctcttcctaa tattataggt caaccagatg aacagggaaa tgtatctaca | 1620 |
| atgggatttc cgtttgaaaa agcttcttat ggaggtacag ttgttaaaga atggttaaat | 1680 |
| ggtgcgaatg cgatgaagct ttctcctggg caatctatag gtattcctat tacaaatgta | 1740 |
| acaagtggag aatatcaaat tcgttgtcgt tatgcaagta atgataatac taacgttttc | 1800 |
| tttaatgtag atactggtgg agcaaatcca attttccaac agataaactt tgcatctact | 1860 |
| gtagataata atacgggagt acaaggagca aatggtgtct atgtagtcaa atctattgct | 1920 |
| acaactgata attcttttac agaaattcct gcgaagacga ttaatgttca tttaaccaac | 1980 |
| caaggttctt ctgatgtctt tttagaccgt attgaattta tacctttttc tctacctctt | 2040 |
| atatatcatg gaagttataa tacttcatca ggtgcagatg atgtttatg gtcttcttca | 2100 |
| aatatgaatt actacgatat aatagtaaat ggtcaggcca atagtagtag tatcgctagt | 2160 |
| tctatgcatt tgcttaataa aggaaaagtg ataaaaacaa ttgatattcc agggcattcg | 2220 |
| gaaaccttct tgctacgtt cccagttcca gaaggattta atgaagttag aattcttgct | 2280 |
| ggccttccag aagttagtgg aaatattacc gtacaatcta ataatccgcc tcaacctagt | 2340 |
| aataatggtg gtggtgatgg tggtggtaat ggtggtggtg atggtggtca atacaatttt | 2400 |

-continued

```
tctttaagcg atctgatca tacgactatt tatcatggaa aacttgaaac tgggattcat    2460
gtacaaggta attataccta tacaggtact cccgtattaa tactgaatgc ttacagaaat    2520
aatactgtag tatcaagcat tccagtatat tctccttttg atataactat acagacagaa    2580
gctgatagcc ttgagcttga actacaacct agatatggtt ttgccacagt gaatggtact    2640
gcaacagtaa aaagtcctaa tgtaaattac gatagatcat ttaaactccc aatagactta    2700
caaaatatca aacacaagt aaatgcatta ttcgcatctg aacacaaaa tatgcttgct    2760 cataatgtaa gtgatcatga tattgaagaa gttgtattaa aagtggatgc cttatcagat    2820
gaagtatttg gagatgagaa gaaggcttta cgtaaattgg tgaatcaagc aaaacgtttg    2880
agtagagcaa gaaatcttct gataggtggg agttttgaaa attgggatgc atggtataaa    2940
ggaagaaatg tagtaactgt atctgatcat gaactattta agagtgatca tgtattatta    3000
ccaccaccag gattgtctcc atcttatatt ttccaaaaag tggaggaatc taaattaaaa    3060
ccaaatacac gttatattgt ttctggattc atcgcacatg gaaaagacct agaaattgtt    3120
gtttcacgtt atgggcaaga agtgcaaaag gtcgtgcaag ttccttatgg agaagcattc    3180
ccgttaacat caaatggacc agtttgttgt cccccacgtt ctacaagtaa tggaacctta    3240
ggagatccac atttctttag ttacagtatc gatgtaggtg cactagattt acaagcaaac    3300
cctggtattg aatttggtct tcgtattgta aatccaactg gaatggcacg cgtaagcaat    3360
ttggaaattc gtgaagatcg tccattagca gcaaatgaaa tacgacaagt acaacgtgtc    3420
gcaagaaatt ggagaaccga gtatgagaaa gaacgtgcgg aagtaacaag tttaattcaa    3480
cctgttatca atcgaatcaa cggattgtat gaaaatggaa attggaacgg ttctattcgt    3540
tcagatattt cgtatcagaa tatagacgcg attgtattac caacgttacc aaagttacgc    3600
cattggttta tgtcagatag attcagtgaa caaggagata taatggctaa attccaaggt    3660
gcattaaatc gtgcgtatgc acaactggaa caaagtacgc ttctgcataa tggtcatttt    3720
acaaaagatg cagctaattg gacaatagaa ggcgatgcac atcagataac actagaagat    3780
ggtagacgtg tattgcgact tccagattgg tcttcgagtg tatctcaaat gattgaaatc    3840 gagaattttta atccagataa agaatacaac ttagtattcc atgggcaagg agaaggaacg    3900
gttacgttgg agcatggaga agaaacaaaa tatatagaaa cgcatacaca tcattttgcg    3960
aattttacaa cttctcaacg tcaaggactc acgtttgaat caaataaagt gacagtgacc    4020
atttcttcag aagatggaga attcttagtg gataatattg cgcttgtgga agctcctctt    4080
cctacagatg accaaaattc tgagggaaat acggcttcca gtacgaatag cgatacaagt    4140
atgaacaaca atcaa                                                    4155
```

<210> SEQ ID NO 2
<211> LENGTH: 1385
<212> TYPE: PRT
<213> ORGANISM: Bacillus thuringiensis

<400> SEQUENCE: 2

```
Met Ala Ile Leu Asn Glu Leu Tyr Pro Ser Val Pro Tyr Asn Val Leu
  1               5                  10                  15

Ala Tyr Thr Pro Pro Ser Phe Leu Pro Asp Ala Gly Thr Gln Ala Thr
             20                  25                  30

Pro Ala Asp Leu Thr Ala Tyr Glu Gln Leu Leu Lys Asn Leu Glu Lys
         35                  40                  45

Gly Ile Asn Ala Gly Thr Tyr Ser Lys Ala Ile Ala Asp Val Leu Lys
```

```
           50                  55                  60
Gly Ile Phe Ile Asp Asp Thr Ile Asn Tyr Gln Thr Tyr Val Asn Ile
 65                  70                  75                  80

Gly Leu Ser Leu Ile Thr Leu Ala Val Pro Glu Ile Gly Ile Phe Thr
                     85                  90                  95

Pro Phe Ile Gly Leu Phe Phe Ala Ala Leu Asn Lys His Asp Ala Pro
                    100                 105                 110

Pro Pro Pro Asn Ala Lys Asp Ile Phe Glu Ala Met Lys Pro Ala Ile
                115                 120                 125

Gln Glu Met Ile Asp Arg Thr Leu Thr Ala Asp Glu Gln Thr Phe Leu
                130                 135                 140

Asn Gly Glu Ile Ser Gly Leu Gln Asn Leu Ala Ala Arg Tyr Gln Ser
145                 150                 155                 160

Thr Met Asp Asp Ile Gln Ser His Gly Gly Phe Asn Lys Val Asp Ser
                    165                 170                 175

Gly Leu Ile Lys Lys Phe Thr Asp Glu Val Leu Ser Leu Asn Ser Phe
                180                 185                 190

Tyr Thr Asp Arg Leu Pro Val Phe Ile Thr Asp Asn Thr Ala Asp Arg
                195                 200                 205

Thr Leu Leu Gly Leu Pro Tyr Tyr Ala Ile Leu Ala Ser Met His Leu
                210                 215                 220

Met Leu Leu Arg Asp Ile Ile Thr Lys Gly Pro Thr Trp Asp Ser Lys
225                 230                 235                 240

Ile Asn Phe Thr Pro Asp Ala Ile Asp Ser Phe Lys Thr Asp Ile Lys
                    245                 250                 255

Asn Asn Ile Lys Leu Tyr Ser Lys Thr Ile Tyr Asp Val Phe Gln Lys
                260                 265                 270

Gly Leu Ala Ser Tyr Gly Thr Pro Ser Asp Leu Glu Ser Phe Ala Lys
                275                 280                 285

Lys Gln Lys Tyr Ile Glu Ile Met Thr Thr His Cys Leu Asp Phe Ala
                290                 295                 300

Arg Leu Phe Pro Thr Phe Asp Pro Asp Leu Tyr Pro Thr Gly Ser Gly
305                 310                 315                 320

Asp Ile Ser Leu Gln Lys Thr Arg Arg Ile Leu Ser Pro Phe Ile Pro
                    325                 330                 335

Ile Arg Thr Ala Asp Gly Leu Thr Leu Asn Asn Thr Ser Ile Asp Thr
                340                 345                 350

Ser Asn Trp Pro Asn Tyr Glu Asn Gly Asn Gly Ala Phe Pro Asn Pro
                355                 360                 365

Lys Glu Arg Ile Leu Lys Gln Phe Lys Leu Tyr Pro Ser Trp Arg Ala
                370                 375                 380

Gly Gln Tyr Gly Gly Leu Leu Gln Pro Tyr Leu Trp Ala Ile Glu Val
385                 390                 395                 400

Gln Asp Ser Val Glu Thr Arg Leu Tyr Gly Gln Leu Pro Ala Val Asp
                    405                 410                 415

Pro Gln Ala Gly Pro Asn Tyr Val Ser Ile Asp Ser Ser Asn Pro Ile
                420                 425                 430

Ile Gln Ile Asn Met Asp Thr Trp Lys Thr Pro Pro Gln Gly Ala Ser
                435                 440                 445

Gly Trp Asn Thr Asn Leu Met Arg Gly Ser Val Ser Gly Leu Ser Phe
                450                 455                 460

Leu Gln Arg Asp Gly Thr Arg Leu Ser Ala Gly Met Gly Gly Gly Phe
465                 470                 475                 480
```

-continued

```
Ala Asp Thr Ile Tyr Ser Leu Pro Ala Thr His Tyr Leu Ser Tyr Leu
            485                 490                 495

Tyr Gly Thr Pro Tyr Gln Thr Ser Asp Asn Tyr Ser Gly His Val Gly
            500                 505                 510

Ala Leu Val Gly Val Ser Thr Pro Gln Glu Ala Thr Leu Pro Asn Ile
            515                 520                 525

Ile Gly Gln Pro Asp Glu Gln Gly Asn Val Ser Thr Met Gly Phe Pro
            530                 535                 540

Phe Glu Lys Ala Ser Tyr Gly Gly Thr Val Val Lys Glu Trp Leu Asn
545                 550                 555                 560

Gly Ala Asn Ala Met Lys Leu Ser Pro Gly Gln Ser Ile Gly Ile Pro
                565                 570                 575

Ile Thr Asn Val Thr Ser Gly Glu Tyr Gln Ile Arg Cys Arg Tyr Ala
                580                 585                 590

Ser Asn Asp Asn Thr Asn Val Phe Phe Asn Val Asp Thr Gly Gly Ala
            595                 600                 605

Asn Pro Ile Phe Gln Gln Ile Asn Phe Ala Ser Thr Val Asp Asn Asn
            610                 615                 620

Thr Gly Val Gln Gly Ala Asn Gly Val Tyr Val Val Lys Ser Ile Ala
625                 630                 635                 640

Thr Thr Asp Asn Ser Phe Thr Glu Ile Pro Ala Lys Thr Ile Asn Val
                645                 650                 655

His Leu Thr Asn Gln Gly Ser Ser Asp Val Phe Leu Asp Arg Ile Glu
                660                 665                 670

Phe Ile Pro Phe Ser Leu Pro Leu Ile Tyr His Gly Ser Tyr Asn Thr
            675                 680                 685

Ser Ser Gly Ala Asp Asp Val Leu Trp Ser Ser Ser Asn Met Asn Tyr
690                 695                 700

Tyr Asp Ile Ile Val Asn Gly Gln Ala Asn Ser Ser Ile Ala Ser
705                 710                 715                 720

Ser Met His Leu Leu Asn Lys Gly Lys Val Ile Lys Thr Ile Asp Ile
                725                 730                 735

Pro Gly His Ser Glu Thr Phe Phe Ala Thr Phe Pro Val Pro Glu Gly
            740                 745                 750

Phe Asn Glu Val Arg Ile Leu Ala Gly Leu Pro Glu Val Ser Gly Asn
            755                 760                 765

Ile Thr Val Gln Ser Asn Asn Pro Pro Gln Pro Ser Asn Asn Gly Gly
            770                 775                 780

Gly Asp Gly Gly Gly Asn Gly Gly Asp Gly Gln Tyr Asn Phe
785                 790                 795                 800

Ser Leu Ser Gly Ser Asp His Thr Thr Ile Tyr His Gly Lys Leu Glu
                805                 810                 815

Thr Gly Ile His Val Gln Gly Asn Tyr Thr Tyr Thr Gly Thr Pro Val
                820                 825                 830

Leu Ile Leu Asn Ala Tyr Arg Asn Asn Thr Val Val Ser Ser Ile Pro
                835                 840                 845

Val Tyr Ser Pro Phe Asp Ile Thr Ile Gln Thr Glu Ala Asp Ser Leu
850                 855                 860

Glu Leu Glu Leu Gln Pro Arg Tyr Gly Phe Ala Thr Val Asn Gly Thr
865                 870                 875                 880

Ala Thr Val Lys Ser Pro Asn Val Asn Tyr Asp Arg Ser Phe Lys Leu
                885                 890                 895
```

-continued

```
Pro Ile Asp Leu Gln Asn Ile Thr Thr Gln Val Asn Ala Leu Phe Ala
            900                 905                 910

Ser Gly Thr Gln Asn Met Leu Ala His Asn Val Ser Asp His Asp Ile
            915                 920                 925

Glu Glu Val Val Leu Lys Val Asp Ala Leu Ser Asp Glu Val Phe Gly
            930                 935                 940

Asp Glu Lys Lys Ala Leu Arg Lys Leu Val Asn Gln Ala Lys Arg Leu
945                 950                 955                 960

Ser Arg Ala Arg Asn Leu Leu Ile Gly Gly Ser Phe Glu Asn Trp Asp
            965                 970                 975

Ala Trp Tyr Lys Gly Arg Asn Val Val Thr Val Ser Asp His Glu Leu
            980                 985                 990

Phe Lys Ser Asp His Val Leu Leu Pro Pro Gly Leu Ser Pro Ser
            995                 1000                1005

Tyr Ile Phe Gln Lys Val Glu Glu Ser Lys Leu Lys Pro Asn Thr Arg
            1010                1015                1020

Tyr Ile Val Ser Gly Phe Ile Ala His Gly Lys Asp Leu Glu Ile Val
            1025                1030                1035                1040

Val Ser Arg Tyr Gly Gln Glu Val Gln Lys Val Val Gln Val Pro Tyr
                1045                1050                1055

Gly Glu Ala Phe Pro Leu Thr Ser Asn Gly Pro Val Cys Cys Pro Pro
                1060                1065                1070

Arg Ser Thr Ser Asn Gly Thr Leu Gly Asp Pro His Phe Phe Ser Tyr
            1075                1080                1085

Ser Ile Asp Val Gly Ala Leu Asp Leu Gln Ala Asn Pro Gly Ile Glu
            1090                1095                1100

Phe Gly Leu Arg Ile Val Asn Pro Thr Gly Met Ala Arg Val Ser Asn
1105                1110                1115                1120

Leu Glu Ile Arg Glu Asp Arg Pro Leu Ala Ala Asn Glu Ile Arg Gln
            1125                1130                1135

Val Gln Arg Val Ala Arg Asn Trp Arg Thr Glu Tyr Glu Lys Glu Arg
            1140                1145                1150

Ala Glu Val Thr Ser Leu Ile Gln Pro Val Ile Asn Arg Ile Asn Gly
            1155                1160                1165

Leu Tyr Glu Asn Gly Asn Trp Asn Gly Ser Ile Arg Ser Asp Ile Ser
    1170                1175                1180

Tyr Gln Asn Ile Asp Ala Ile Val Leu Pro Thr Leu Pro Lys Leu Arg
1185                1190                1195                1200

His Trp Phe Met Ser Asp Arg Phe Ser Glu Gln Gly Asp Ile Met Ala
            1205                1210                1215

Lys Phe Gln Gly Ala Leu Asn Arg Ala Tyr Ala Gln Leu Glu Gln Ser
            1220                1225                1230

Thr Leu Leu His Asn Gly His Phe Thr Lys Asp Ala Ala Asn Trp Thr
            1235                1240                1245

Ile Glu Gly Asp Ala His Gln Ile Thr Leu Glu Asp Gly Arg Arg Val
            1250                1255                1260

Leu Arg Leu Pro Asp Trp Ser Ser Ser Val Ser Gln Met Ile Glu Ile
1265                1270                1275                1280

Glu Asn Phe Asn Pro Asp Lys Glu Tyr Asn Leu Val Phe His Gly Gln
            1285                1290                1295

Gly Glu Gly Thr Val Thr Leu Glu His Gly Glu Glu Thr Lys Tyr Ile
                1300                1305                1310

Glu Thr His Thr His His Phe Ala Asn Phe Thr Thr Ser Gln Arg Gln
```

-continued

```
      1315                1320                1325

Gly Leu Thr Phe Glu Ser Asn Lys Val Thr Val Thr Ile Ser Ser Glu
   1330                1335                1340

Asp Gly Glu Phe Leu Val Asp Asn Ile Ala Leu Val Glu Ala Pro Leu
1345                1350                1355                1360

Pro Thr Asp Asp Gln Asn Ser Glu Gly Asn Thr Ala Ser Ser Thr Asn
                1365                1370                1375

Ser Asp Thr Ser Met Asn Asn Asn Gln
            1380                1385

<210> SEQ ID NO 3
<211> LENGTH: 3867
<212> TYPE: DNA
<213> ORGANISM: Bacillus thuringiensis

<400> SEQUENCE: 3
atggcaattt taaatgaatt atatccatct gtaccttata atgtattggc gtatacgcca     60
ccctcttttt tacctgatgc gggtacacaa gctacacctg ctgacttaac agcttatgaa    120
caattgttga aaaatttaga aaaagggata aatgctggaa cttattcgaa agcaatagct    180
gatgtactta aaggtatttt tatagatgat acaataaatt atcaaacata tgtaaatatt    240
ggtttaagtt taattacatt agctgtaccg gaaattggta tttttacacc tttcatcggt    300 ttgtttttg ctgcattgaa taaacatgat gctccacctc ctcctaatgc aaaagatata    360
tttgaggcta tgaaaccagc gattcaagag atgattgata gaactttaac tgcggatgag    420
caaacatttt taaatgggga aataagtggt ttacaaaatt tagcagcaag ataccagtct    480
acaatggatg atattcaaag ccatggagga tttaataagg tagattctgg attaattaaa    540
aagtttacag atgaggtact atctttaaat agtttttata cagatcgttt acctgtattt    600
attacagata atacagcgga tcgaactttg ttaggtcttc cttattatgc tatacttgcg    660
agcatgcatc ttatgttatt aagagatatc attactaagg gtccgacatg ggattctaaa    720
attaatttca caccagatgc aattgattcc tttaaaaccg atattaaaaa taatataaag    780
ctttactcta aaactattta tgacgtattt cagaagggac ttgcttcata cggaacgcct    840
tctgatttag agtcctttgc aaaaaaacaa aaatatattg aaattatgac aacacattgt    900
ttagattttg caagattgtt tcctactttt gatccagatc tttatccaac aggatcaggt    960
gatataagtt tacaaaaaac acgtagaatt ctttctcctt ttatccctat acgtactgca   1020
gatgggttaa cattaaataa tacttcaatt gatacttcaa attggcctaa ttatgaaaat   1080
gggaatggcg cgtttccaaa cccaaaagaa agaatattaa aacaattcaa actgtatcct   1140
agttggagag cggcacagta cggtgggctt ttacaacctt atttatgggc aatagaagtc   1200
caagattctg tagagactcg tttgtatggg cagcttccag ctgtagatcc acaggcaggg   1260
cctaattatg tttccataga ttcttctaat ccaatcatac aaataaatat ggatacttgg   1320
aaaacaccac cacaaggtgc gagtgggtgg aatacaaatt taatgagagg aagtgtaagc   1380
gggttaagtt ttttacaacg agatggtacg agacttagtg ctggtatggg tggtggtttt   1440
gctgatacaa tatatagtct ccctgcaact cattatcttt cttatctcta tggaactcct   1500
tatcaaactt ctgataacta ttctggtcac gttggtgcat tggtaggtgt gagtacgcct   1560
caagaggcta ctcttcctaa tattataggt caaccagatg aacagggaaa tgtatctaca   1620
atgggatttc cgtttgaaaa agcttcttat ggaggtacag ttgttaaaga atggttaaat   1680
ggtgcgaatg cgatgaagct ttctcctggg caatctatag gtattcctat tacaaatgta   1740
```

-continued

```
acaagtggag aatatcaaat tcgttgtcgt tatgcaagta atgataatac taacgttttc    1800
tttaatgtag atactggtgg agcaaatcca attttccaac agataaactt tgcatctact    1860
gtagataata atacgggagt acaaggagca aatggtgtct atgtagtcaa atctattgct    1920
acaactgata attcttttac agtaaaaatt cctgcgaaga cgattaatgt tcatttaacc    1980
aaccaaggtt cttctgatgt cttttagat cgtattgagt ttgttccaat tctagaatca     2040
aatactgtaa ctatattcaa caattcatat actacaggtt cagcaaatct tataccagca    2100
atagctcctc tttggagtac tagttcagat aaagccctta caggttctat gtcaataaca    2160
ggtcgaacta cccctaacag tgatgatgct ttgcttcgat tttttaaaac taattatgat    2220
acacaaacca ttcctattcc gggttccgga aaagatttta caaatactct agaaatacaa    2280
gacatagttt ctattgatat ttttgtcgga tctggtctac atggatccga tggatctata    2340
aaattagatt ttaccaataa taatagtggt agtggtggcc ctccaaagag tttcaccgag    2400
caaaatgatt tagagaatat cacaacacaa gtgaatgctc tattcacatc taatacacaa    2460
gatgcacttg caacagatgt gagtgatcat gatattgaag aagtggttct aaaagtagat    2520
gcattatctg atgaagtgtt tggaaaagag aaaaaaacat tgcgtaaatt tgtaaatcaa    2580
gcgaagcgct taagcaaggc gcgtaatctc ctggtaggag gcaattttga taacttggat    2640
gcttggtata gaggaagaaa tgtagtaaac gtatctaatc acgaactgtt gaagagtgat    2700
catgtattat taccaccacc aggattgtct ccatcttata ttttccaaaa agtggaggaa    2760
tctaaattaa aacgaaatac acgttatacg gtttctggat ttattgcgca tgcaacagat    2820
ttagaaattg tggtttctcg ttatgggcaa gaaataaaga aagtggtgca agttcccttat   2880 ggagaagcat tcccattaac atcaagtgga ccagtttgtt gtatcccaca ttctacaagt    2940
aatgaaactt taggcaatcc acatttcttt agttacagta ttgatgtagg tgcattagat    3000
gtagacacaa accctggtat tgaattcggt cttcgtattg taaatccaac tggaatggca    3060
cgcgtaagca atttggaaat tcgtgaagat cgtccattag cagcaaatga atacgacaa     3120 gtacaacgtg tcgcaagaaa ttggagaacc gagtatgaga agaacgtgc ggaagtaaca     3180 agtttaattc aacctgttat caatcgaatc aatggattgt atgacaatgg aaattggaac    3240
ggttctattc gttcagatat ttcgtatcag aatatagacg cgattgtatt accaacgtta    3300
ccaaagttac gccattggtt tatgtcagat agatttagtg aacaaggaga tatcatggct    3360
aaattccaag gtgcattaaa tcgtgcgtat gcacaactgg aacaaaatac gcttctgcat    3420
aatggtcatt ttacaaaaga tgcagccaat tggacggtag aaggcgatgc acatcaggta    3480
gtattagaag atggtaaacg tgtattacga ttgccagatt ggtcttcgag tgtgtctcaa    3540
acgattgaaa tcgagaattt tgatccagat aaagaatatc aattagtatt tcatgggcaa    3600
ggagaaggaa cggttacgtt ggagcatgga gaagaaacaa aatatataga aacgcataca    3660
catcattttg cgaattttac aacttctcaa cgtcaaggac tcacgtttga atcaaataaa    3720
gtgacagtga ccatttcttc agaagatgga gaattcttag tggataatat tgcgcttgtg    3780
gaagctcctc ttcctacaga tgaccaaaat tctgagggaa atacggcttc cagtacgaat    3840
agcgatacaa gtatgaacaa caatcaa                                        3867
```

<210> SEQ ID NO 4
<211> LENGTH: 1289
<212> TYPE: PRT
<213> ORGANISM: Bacillus thuringiensis -continued

```
<400> SEQUENCE: 4

Met Ala Ile Leu Asn Glu Leu Tyr Pro Ser Val Pro Tyr Asn Val Leu
 1               5                  10                  15

Ala Tyr Thr Pro Pro Ser Phe Leu Pro Asp Ala Gly Thr Gln Ala Thr
             20                  25                  30

Pro Ala Asp Leu Thr Ala Tyr Glu Gln Leu Leu Lys Asn Leu Glu Lys
         35                  40                  45

Gly Ile Asn Ala Gly Thr Tyr Ser Lys Ala Ile Ala Asp Val Leu Lys
     50                  55                  60

Gly Ile Phe Ile Asp Asp Thr Ile Asn Tyr Gln Thr Tyr Val Asn Ile
 65                  70                  75                  80

Gly Leu Ser Leu Ile Thr Leu Ala Val Pro Glu Ile Gly Ile Phe Thr
                 85                  90                  95

Pro Phe Ile Gly Leu Phe Phe Ala Ala Leu Asn Lys His Asp Ala Pro
            100                 105                 110

Pro Pro Pro Asn Ala Lys Asp Ile Phe Glu Ala Met Lys Pro Ala Ile
        115                 120                 125

Gln Glu Met Ile Asp Arg Thr Leu Thr Ala Asp Glu Gln Thr Phe Leu
    130                 135                 140

Asn Gly Glu Ile Ser Gly Leu Gln Asn Leu Ala Ala Arg Tyr Gln Ser
145                 150                 155                 160

Thr Met Asp Asp Ile Gln Ser His Gly Gly Phe Asn Lys Val Asp Ser
                165                 170                 175

Gly Leu Ile Lys Lys Phe Thr Asp Glu Val Leu Ser Leu Asn Ser Phe
            180                 185                 190

Tyr Thr Asp Arg Leu Pro Val Phe Ile Thr Asp Asn Thr Ala Asp Arg
        195                 200                 205

Thr Leu Leu Gly Leu Pro Tyr Tyr Ala Ile Leu Ala Ser Met His Leu
    210                 215                 220

Met Leu Leu Arg Asp Ile Ile Thr Lys Gly Pro Thr Trp Asp Ser Lys
225                 230                 235                 240

Ile Asn Phe Thr Pro Asp Ala Ile Asp Ser Phe Lys Thr Asp Ile Lys
                245                 250                 255

Asn Asn Ile Lys Leu Tyr Ser Lys Thr Ile Tyr Asp Val Phe Gln Lys
            260                 265                 270

Gly Leu Ala Ser Tyr Gly Thr Pro Ser Asp Leu Glu Ser Phe Ala Lys
        275                 280                 285

Lys Gln Lys Tyr Ile Glu Ile Met Thr Thr His Cys Leu Asp Phe Ala
    290                 295                 300

Arg Leu Phe Pro Thr Phe Asp Pro Asp Leu Tyr Pro Thr Gly Ser Gly
305                 310                 315                 320

Asp Ile Ser Leu Gln Lys Thr Arg Arg Ile Leu Ser Pro Phe Ile Pro
                325                 330                 335

Ile Arg Thr Ala Asp Gly Leu Thr Leu Asn Asn Thr Ser Ile Asp Thr
            340                 345                 350

Ser Asn Trp Pro Asn Tyr Glu Asn Gly Asn Gly Ala Phe Pro Asn Pro
        355                 360                 365

Lys Glu Arg Ile Leu Lys Gln Phe Lys Leu Tyr Pro Ser Trp Arg Ala
    370                 375                 380

Ala Gln Tyr Gly Gly Leu Leu Gln Pro Tyr Leu Trp Ala Ile Glu Val
385                 390                 395                 400

Gln Asp Ser Val Glu Thr Arg Leu Tyr Gly Gln Leu Pro Ala Val Asp
                405                 410                 415
```

-continued

```
Pro Gln Ala Gly Pro Asn Tyr Val Ser Ile Asp Ser Ser Asn Pro Ile
            420                 425                 430
Ile Gln Ile Asn Met Asp Thr Trp Lys Thr Pro Pro Gln Gly Ala Ser
        435                 440                 445
Gly Trp Asn Thr Asn Leu Met Arg Gly Ser Val Ser Gly Leu Ser Phe
450                 455                 460
Leu Gln Arg Asp Gly Thr Arg Leu Ser Ala Gly Met Gly Gly Gly Phe
465                 470                 475                 480
Ala Asp Thr Ile Tyr Ser Leu Pro Ala Thr His Tyr Leu Ser Tyr Leu
            485                 490                 495
Tyr Gly Thr Pro Tyr Gln Thr Ser Asp Asn Tyr Ser Gly His Val Gly
            500                 505                 510
Ala Leu Val Gly Val Ser Thr Pro Gln Glu Ala Thr Leu Pro Asn Ile
            515                 520                 525
Ile Gly Gln Pro Asp Glu Gln Gly Asn Val Ser Thr Met Gly Phe Pro
            530                 535                 540
Phe Glu Lys Ala Ser Tyr Gly Gly Thr Val Val Lys Glu Trp Leu Asn
545                 550                 555                 560
Gly Ala Asn Ala Met Lys Leu Ser Pro Gly Gln Ser Ile Gly Ile Pro
            565                 570                 575
Ile Thr Asn Val Thr Ser Gly Glu Tyr Gln Ile Arg Cys Arg Tyr Ala
            580                 585                 590
Ser Asn Asp Asn Thr Asn Val Phe Phe Asn Val Asp Thr Gly Gly Ala
            595                 600                 605
Asn Pro Ile Phe Gln Gln Ile Asn Phe Ala Ser Thr Val Asp Asn Asn
            610                 615                 620
Thr Gly Val Gln Gly Ala Asn Gly Val Tyr Val Val Lys Ser Ile Ala
625                 630                 635                 640
Thr Thr Asp Asn Ser Phe Thr Val Lys Ile Pro Ala Lys Thr Ile Asn
            645                 650                 655
Val His Leu Thr Asn Gln Gly Ser Ser Asp Val Phe Leu Asp Arg Ile
            660                 665                 670
Glu Phe Val Pro Ile Leu Glu Ser Asn Thr Val Thr Ile Phe Asn Asn
            675                 680                 685
Ser Tyr Thr Thr Gly Ser Ala Asn Leu Ile Pro Ala Ile Ala Pro Leu
            690                 695                 700
Trp Ser Thr Ser Ser Asp Lys Ala Leu Thr Gly Ser Met Ser Ile Thr
705                 710                 715                 720
Gly Arg Thr Thr Pro Asn Ser Asp Asp Ala Leu Leu Arg Phe Phe Lys
            725                 730                 735
Thr Asn Tyr Asp Thr Gln Thr Ile Pro Ile Pro Gly Ser Gly Lys Asp
            740                 745                 750
Phe Thr Asn Thr Leu Glu Ile Gln Asp Ile Val Ser Ile Asp Ile Phe
            755                 760                 765
Val Gly Ser Gly Leu His Gly Ser Asp Gly Ser Ile Lys Leu Asp Phe
            770                 775                 780
Thr Asn Asn Asn Ser Gly Ser Gly Gly Ser Pro Lys Ser Phe Thr Glu
785                 790                 795                 800
Gln Asn Asp Leu Glu Asn Ile Thr Thr Gln Val Asn Ala Leu Phe Thr
            805                 810                 815
Ser Asn Thr Gln Asp Ala Leu Ala Thr Asp Val Ser Asp His Asp Ile
            820                 825                 830
```

```
Glu Glu Val Val Leu Lys Val Asp Ala Leu Ser Asp Glu Val Phe Gly
            835                 840                 845
Lys Glu Lys Lys Thr Leu Arg Lys Phe Val Asn Gln Ala Lys Arg Leu
    850                 855                 860
Ser Lys Ala Arg Asn Leu Leu Val Gly Gly Asn Phe Asp Asn Leu Asp
865                 870                 875                 880
Ala Trp Tyr Arg Gly Arg Asn Val Asn Val Ser Asn His Glu Leu
                885                 890                 895
Leu Lys Ser Asp His Val Leu Leu Pro Pro Gly Leu Ser Pro Ser
            900                 905                 910
Tyr Ile Phe Gln Lys Val Glu Glu Ser Lys Leu Lys Arg Asn Thr Arg
        915                 920                 925
Tyr Thr Val Ser Gly Phe Ile Ala His Ala Thr Asp Leu Glu Ile Val
    930                 935                 940
Val Ser Arg Tyr Gly Gln Glu Ile Lys Lys Val Val Gln Val Pro Tyr
945                 950                 955                 960
Gly Glu Ala Phe Pro Leu Thr Ser Ser Gly Pro Val Cys Cys Ile Pro
                965                 970                 975
His Ser Thr Ser Asn Gly Thr Leu Gly Asn Pro His Phe Phe Ser Tyr
            980                 985                 990
Ser Ile Asp Val Gly Ala Leu Asp Val Asp Thr Asn Pro Gly Ile Glu
        995                 1000                1005
Phe Gly Leu Arg Ile Val Asn Pro Thr Gly Met Ala Arg Val Ser Asn
    1010                1015                1020
Leu Glu Ile Arg Glu Asp Arg Pro Leu Ala Ala Asn Glu Ile Arg Gln
1025                1030                1035                1040
Val Gln Arg Val Ala Arg Asn Trp Arg Thr Glu Tyr Glu Lys Glu Arg
                1045                1050                1055
Ala Glu Val Thr Ser Leu Ile Gln Pro Val Ile Asn Arg Ile Asn Gly
            1060                1065                1070
Leu Tyr Asp Asn Gly Asn Trp Asn Gly Ser Ile Arg Ser Asp Ile Ser
        1075                1080                1085
Tyr Gln Asn Ile Asp Ala Ile Val Leu Pro Thr Leu Pro Lys Leu Arg
    1090                1095                1100
His Trp Phe Met Ser Asp Arg Phe Ser Glu Gln Gly Asp Ile Met Ala
1105                1110                1115                1120
Lys Phe Gln Gly Ala Leu Asn Arg Ala Tyr Ala Gln Leu Glu Gln Asn
                1125                1130                1135
Thr Leu Leu His Asn Gly His Phe Thr Lys Asp Ala Ala Asn Trp Thr
            1140                1145                1150
Val Glu Gly Asp Ala His Gln Val Val Leu Glu Asp Gly Lys Arg Val
        1155                1160                1165
Leu Arg Leu Pro Asp Trp Ser Ser Ser Val Ser Gln Thr Ile Glu Ile
    1170                1175                1180
Glu Asn Phe Asp Pro Asp Lys Glu Tyr Gln Leu Val Phe His Gly Gln
1185                1190                1195                1200
Gly Glu Gly Thr Val Thr Leu Glu His Gly Glu Glu Thr Lys Tyr Ile
                1205                1210                1215
Glu Thr His Thr His His Phe Ala Asn Phe Thr Thr Ser Gln Arg Gln
            1220                1225                1230
Gly Leu Thr Phe Glu Ser Asn Lys Val Thr Val Thr Ile Ser Ser Glu
        1235                1240                1245
Asp Gly Glu Phe Leu Val Asp Asn Ile Ala Leu Val Glu Ala Pro Leu
```

-continued

```
  1250                1255                1260

Pro Thr Asp Asp Gln Asn Ser Glu Gly Asn Thr Ala Ser Ser Thr Asn
1265                1270                1275                1280

Ser Asp Thr Ser Met Asn Asn Asn Gln
               1285

<210> SEQ ID NO 5
<211> LENGTH: 3771
<212> TYPE: DNA
<213> ORGANISM: Bacillus thuringiensis
<220> FEATURE:
<221> NAME/KEY: misc_feature
<222> LOCATION: (4)..(24)
<223> OTHER INFORMATION: /function- "oligonucleotide
      hybridization probe"
      /product= "GCA/T ACA/T TTA AAT GAA GTA/T TAT"
      /standard_name=  "probe a"  /note= "Probe A"
<220> FEATURE:
<221> NAME/KEY: misc_feature
<222> LOCATION: (13)..(33)
<223> OTHER INFORMATION: /function= "oligonucleotide
      hybridization probe"
      /product= "AAT GAA GTA/T TAT CCA/T GTA/T AAT"
      /standard_name= "Probe B" /label= probe-b /note-
      "probe b"

<400> SEQUENCE: 5
atggctacac ttaatgaagt atatcctgtg aattataatg tattatcttc tgatgctttt      60
caacaattag atacaacagg ttttaaaagt aaatatgatg aaatgataaa agcattcgaa     120
aaaaaatgga aaaaaggggc aaaaggaaaa gacctttttag atgttgcatg gacttatata     180
actacaggag aaattgaccc tttaaatgta attaaaggtg ttttatctgt attaacttta     240
attcctgaag ttggtactgt ggcctctgca gcaagtacta ttgtaagttt tatttggcct     300
aaaatatttg gagataaacc aaatgcaaaa aatatatttg aagagctcaa gcctcaaatt     360
gaagcattaa ttcaacaaga tataacaaac tatcaagatg caattaatca aaaaaaattt     420
gacagtcttc agaaaacaat taatctatat acagtagcta tagataacaa tgattacgta     480
acagcaaaaa cgcaactcga aatctaaat tctatactta cctcagatat ctccatattt     540
attccagaag gatatgaaac tggaggttta ccttattatg ctatggttgc taatgctcat     600
atattattgt taagagacgc tatagttaat gcagagaaat taggctttag tgataaagaa     660
gtagacacac ataaaaaata tatcaaaatg acaatacaca atcatactga agcagtaata     720
aaagcattct taaatggact tgacaaattt aagagtttag atgtaaatag ctataataaa     780
aaagcaaatt atattaaagg tatgacagaa atggttcttg atctagttgc tctatggcca     840
actttcgatc cagatcatta tcaaaaagaa gtagaaattg aatttacaag aactatttct     900
tctccaattt accaacctgt acctaaaaac atgcaaaata cctctagctc tattgtacct     960
agcgatctat ttcactatca aggagatctt gtaaaattag aattttctac aagaacggac    1020
aacgatggtc ttgcaaaaat ttttactggt attcgaaaca cattctacaa atcgcctaat    1080
actcatgaaa cataccatgt agattttagt tataataccc aatctagtgg taatatttca    1140
agaggctctt caaatccgat tccaattgat cttaataatc ccattatttc aacttgtatt    1200
agaaattcat tttataaggc aatagcggga tcttctgttt tagttaattt taaagatggc    1260
actcaagggt atgcatttgc ccaagcacca acaggaggtg cctgggacca ttcttttatt    1320
gaatctgatg gtgccccaga agggcataaa ttaaactata tttatacttc tccaggtgat    1380
acattaagag atttcatcaa tgtatatact cttataagta ctccaactat aaatgaacta    1440
```

-continued

```
tcaacagaaa aaatcaaagg ctttcctgcg gaaaaaggat atatcaaaaa tcaagggatc    1500
atgaaatatt acgtaaacc agaatatatt aatggagctc aaccagttaa tctggaaaac     1560
cagcaaacat taatattcga atttcatgct tcaaaaacag ctcaatatac cattcgtata    1620
cgttatgcca gtacccaagg aacaaaaggt tattttcgtt tagataatca ggaactgcaa    1680
acgcttaata tacctacttc acacaacggt tatgtaaccg gtaatattgg tgaaaattat    1740
gatttatata caataggttc atatacaatt acagaaggta accatactct tcaaatccaa    1800
cataatgata aaaatggaat ggttttagat cgtattgaat tgttcctaa agattcactt     1860 caagattcac ctcaagattc acctccagaa gttcacgaat caacaattat ttttgataaa    1920
tcatctccaa ctatatggtc ttctaacaaa cactcatata gccatataca tttagaagga    1980
tcatatacaa gtcagggaag ttatccacac aatttattaa ttaatttatt tcatcctaca    2040
gaccctaaca gaaatcatac tattcatgtt aacaatggtg atatgaatgt tgattatgga    2100
aaagattctg tagccgatgg gttaaatttt aataaaataa ctgctacgat accaagtgat    2160
gcttggtata gcggtactat tacttctatg cacttattta atgataataa ttttaaaaca    2220
ataactccta aatttgaact ttctaatgaa ttagaaaaca tcacaactca agtaaatgct    2280
ttattcgcat ctagtgcaca agatactctc gcaagtaatg taagtgatta ctggattgaa    2340
caggtcgtta tgaaagtcga tgccttatca gatgaagtat ttggaaaaga gaaaaaagca    2400
ttacgtaaat tggtaaatca agcaaaacgt ctcagtaaaa tacgaaatct tctcataggt    2460
ggtaattttg acaatttagt cgcttggtat atgggaaaag atgtagtaaa agaatcggat    2520
catgaattat ttaaaagtga tcatgtctta ctacctcccc caacattcca tccttcttat    2580
attttccaaa aggtggaaga atcaaaacta aaaccaaata cacgttatac tatttctggt    2640
tttatcgcac atggagaaga tgtagagctt gttgtctctc gttatgggca agaaatacaa    2700
aaagtgatgc aagtgccata tgaagaagca cttcctctta catctgaatc taattctagt    2760
tgttgtgttc caaatttaaa tataaatgaa acactagctg atccacattt ctttagttat    2820
agcatcgatg ttggttctct ggaaatggaa gcgaatcctg gtattgaatt tggtctccgt    2880
attgtcaaac caacaggtat ggcacgtgta agtaatttag aaattcgaga agaccgtcca    2940
ttaacagcaa aagaaattcg tcaagtacaa cgtgcagcaa gagattggaa acaaaactat    3000
gaacaagaac gaacagagat cacagctata attcaacctg ttcttaatca aattaatgcg    3060
ttatacgaaa atgaagattg gaatggttct attcgttcaa atgtttccta tcatgatcta    3120
gagcaaatta tgcttcctac tttattaaaa actgaggaaa taaattgtaa ttatgatcat    3180
ccagcttttt tattaaaagt atatcattgg tttatgacag atcgtatagg agaacatggt    3240
actattttag cacgtttcca agaagcatta gatcgtgcat atacacaatt agaaagtcgt    3300
aatctcctgc ataacggtca ttttacaact gatacagcga attggacaat agaaggagat    3360
gcccatcata caatcttaga agatggtaga cgtgtgttac gtttaccaga ttggtcttct    3420
aatgcaactc aaacaattga aattgaagat tttgacttag atcaagaata ccaattgctc    3480
attcatgcaa aaggaaaagg ttccattact ttacaacatg gagaagaaaa cgaatatgtg    3540
gaaacacata ctcatcatac aaatgatttt ataacatccc aaaatattcc tttcactttt    3600
aaaggaaatc aaattgaagt ccatattact tcagaagatg gagagttttt aatcgatcac    3660
attacagtaa tagaagtttc taaaacagac acaaatacaa atattattga aaattcacca    3720
atcaatacaa gtatgaatag taatgtaaga gtagatatac caagaagtct c             3771
```

-continued

<210> SEQ ID NO 6
<211> LENGTH: 1257
<212> TYPE: PRT
<213> ORGANISM: Bacillus thuringiensis

<400> SEQUENCE: 6

Met Ala Thr Leu Asn Glu Val Tyr Pro Val Asn Tyr Asn Val Leu Ser
1               5                   10                  15

Ser Asp Ala Phe Gln Gln Leu Asp Thr Thr Gly Phe Lys Ser Lys Tyr
            20                  25                  30

Asp Glu Met Ile Lys Ala Phe Glu Lys Lys Trp Lys Lys Gly Ala Lys
        35                  40                  45

Gly Lys Asp Leu Leu Asp Val Ala Trp Thr Tyr Ile Thr Thr Gly Glu
    50                  55                  60

Ile Asp Pro Leu Asn Val Ile Lys Gly Val Leu Ser Val Leu Thr Leu
65                  70                  75                  80

Ile Pro Glu Val Gly Thr Val Ala Ser Ala Ala Ser Thr Ile Val Ser
                85                  90                  95

Phe Ile Trp Pro Lys Ile Phe Gly Asp Lys Pro Asn Ala Lys Asn Ile
            100                 105                 110

Phe Glu Glu Leu Lys Pro Gln Ile Glu Ala Leu Ile Gln Gln Asp Ile
        115                 120                 125

Thr Asn Tyr Gln Asp Ala Ile Asn Gln Lys Lys Phe Asp Ser Leu Gln
    130                 135                 140

Lys Thr Ile Asn Leu Tyr Thr Val Ala Ile Asp Asn Asn Asp Tyr Val
145                 150                 155                 160

Thr Ala Lys Thr Gln Leu Glu Asn Leu Asn Ser Ile Leu Thr Ser Asp
                165                 170                 175

Ile Ser Ile Phe Ile Pro Glu Gly Tyr Glu Thr Gly Gly Leu Pro Tyr
            180                 185                 190

Tyr Ala Met Val Ala Asn Ala His Ile Leu Leu Leu Arg Asp Ala Ile
        195                 200                 205

Val Asn Ala Glu Lys Leu Gly Phe Ser Asp Lys Glu Val Asp Thr His
    210                 215                 220

Lys Lys Tyr Ile Lys Met Thr Ile His Asn His Thr Glu Ala Val Ile
225                 230                 235                 240

Lys Ala Phe Leu Asn Gly Leu Asp Lys Phe Lys Ser Leu Asp Val Asn
                245                 250                 255

Ser Tyr Asn Lys Lys Ala Asn Tyr Ile Lys Gly Met Thr Glu Met Val
            260                 265                 270

Leu Asp Leu Val Ala Leu Trp Pro Thr Phe Asp Pro Asp His Tyr Gln
        275                 280                 285

Lys Glu Val Glu Ile Glu Phe Thr Arg Thr Ile Ser Ser Pro Ile Tyr
    290                 295                 300

Gln Pro Val Pro Lys Asn Met Gln Asn Thr Ser Ser Ser Ile Val Pro
305                 310                 315                 320

Ser Asp Leu Phe His Tyr Gln Gly Asp Leu Val Lys Leu Glu Phe Ser
                325                 330                 335

Thr Arg Thr Asp Asn Asp Gly Leu Ala Lys Ile Phe Thr Gly Ile Arg
            340                 345                 350

Asn Thr Phe Tyr Lys Ser Pro Asn Thr His Glu Thr Tyr His Val Asp
        355                 360                 365

Phe Ser Tyr Asn Thr Gln Ser Ser Gly Asn Ile Ser Arg Gly Ser Ser
    370                 375                 380

-continued

```
Asn Pro Ile Pro Ile Asp Leu Asn Asn Pro Ile Ile Ser Thr Cys Ile
385                 390                 395                 400

Arg Asn Ser Phe Tyr Lys Ala Ile Ala Gly Ser Ser Val Leu Val Asn
            405                 410                 415

Phe Lys Asp Gly Thr Gln Gly Tyr Ala Phe Ala Gln Ala Pro Thr Gly
            420                 425                 430

Gly Ala Trp Asp His Ser Phe Ile Glu Ser Asp Gly Ala Pro Glu Gly
            435                 440                 445

His Lys Leu Asn Tyr Ile Tyr Thr Ser Pro Gly Asp Thr Leu Arg Asp
450                 455                 460

Phe Ile Asn Val Tyr Thr Leu Ile Ser Thr Pro Thr Ile Asn Glu Leu
465                 470                 475                 480

Ser Thr Glu Lys Ile Lys Gly Phe Pro Ala Glu Lys Gly Tyr Ile Lys
                485                 490                 495

Asn Gln Gly Ile Met Lys Tyr Tyr Gly Lys Pro Glu Tyr Ile Asn Gly
                500                 505                 510

Ala Gln Pro Val Asn Leu Glu Asn Gln Gln Thr Leu Ile Phe Glu Phe
            515                 520                 525

His Ala Ser Lys Thr Ala Gln Tyr Thr Ile Arg Ile Arg Tyr Ala Ser
530                 535                 540

Thr Gln Gly Thr Lys Gly Tyr Phe Arg Leu Asp Asn Gln Glu Leu Gln
545                 550                 555                 560

Thr Leu Asn Ile Pro Thr Ser His Asn Gly Tyr Val Thr Gly Asn Ile
                565                 570                 575

Gly Glu Asn Tyr Asp Leu Tyr Thr Ile Gly Ser Tyr Thr Ile Thr Glu
                580                 585                 590

Gly Asn His Thr Leu Gln Ile Gln His Asn Asp Lys Asn Gly Met Val
            595                 600                 605

Leu Asp Arg Ile Glu Phe Val Pro Lys Asp Ser Leu Gln Asp Ser Pro
610                 615                 620

Gln Asp Ser Pro Pro Glu Val His Glu Ser Thr Ile Ile Phe Asp Lys
625                 630                 635                 640

Ser Ser Pro Thr Ile Trp Ser Ser Asn Lys His Ser Tyr Ser His Ile
                645                 650                 655

His Leu Glu Gly Ser Tyr Thr Ser Gln Gly Ser Tyr Pro His Asn Leu
                660                 665                 670

Leu Ile Asn Leu Phe His Pro Thr Asp Pro Asn Arg Asn His Thr Ile
            675                 680                 685

His Val Asn Asn Gly Asp Met Asn Val Asp Tyr Gly Lys Asp Ser Val
690                 695                 700

Ala Asp Gly Leu Asn Phe Asn Lys Ile Thr Ala Thr Ile Pro Ser Asp
705                 710                 715                 720

Ala Trp Tyr Ser Gly Thr Ile Thr Ser Met His Leu Phe Asn Asp Asn
                725                 730                 735

Asn Phe Lys Thr Ile Thr Pro Lys Phe Glu Leu Ser Asn Glu Leu Glu
            740                 745                 750

Asn Ile Thr Thr Gln Val Asn Ala Leu Phe Ala Ser Ala Gln Asp
            755                 760                 765

Thr Leu Ala Ser Asn Val Ser Asp Tyr Trp Ile Glu Gln Val Val Met
770                 775                 780

Lys Val Asp Ala Leu Ser Asp Glu Val Phe Gly Lys Glu Lys Lys Ala
785                 790                 795                 800

Leu Arg Lys Leu Val Asn Gln Ala Lys Arg Leu Ser Lys Ile Arg Asn
```

-continued

```
                805                 810                 815
Leu Leu Ile Gly Gly Asn Phe Asp Asn Leu Val Ala Trp Tyr Met Gly
            820                 825                 830

Lys Asp Val Val Lys Glu Ser Asp His Glu Leu Phe Lys Ser Asp His
        835                 840                 845

Val Leu Leu Pro Pro Pro Thr Phe His Pro Ser Tyr Ile Phe Gln Lys
850                 855                 860

Val Glu Glu Ser Lys Leu Lys Pro Asn Thr Arg Tyr Thr Ile Ser Gly
865                 870                 875                 880

Phe Ile Ala His Gly Glu Asp Val Glu Leu Val Ser Arg Tyr Gly
            885                 890                 895

Gln Glu Ile Gln Lys Val Met Gln Val Pro Tyr Glu Glu Ala Leu Pro
            900                 905                 910

Leu Thr Ser Glu Ser Asn Ser Ser Cys Cys Val Pro Asn Leu Asn Ile
            915                 920                 925

Asn Glu Thr Leu Ala Asp Pro His Phe Phe Ser Tyr Ser Ile Asp Val
            930                 935                 940

Gly Ser Leu Glu Met Glu Ala Asn Pro Gly Ile Glu Phe Gly Leu Arg
945                 950                 955                 960

Ile Val Lys Pro Thr Gly Met Ala Arg Val Ser Asn Leu Glu Ile Arg
            965                 970                 975

Glu Asp Arg Pro Leu Thr Ala Lys Glu Ile Arg Gln Val Gln Arg Ala
            980                 985                 990

Ala Arg Asp Trp Lys Gln Asn Tyr Glu Gln Glu Arg Thr Glu Ile Thr
            995                 1000                1005

Ala Ile Ile Gln Pro Val Leu Asn Gln Ile Asn Ala Leu Tyr Glu Asn
    1010                1015                1020

Glu Asp Trp Asn Gly Ser Ile Arg Ser Asn Val Ser Tyr His Asp Leu
1025                1030                1035                1040

Glu Gln Ile Met Leu Pro Thr Leu Leu Lys Thr Glu Glu Ile Asn Cys
            1045                1050                1055

Asn Tyr Asp His Pro Ala Phe Leu Leu Lys Val Tyr Arg Trp Phe Met
            1060                1065                1070

Thr Asp Arg Ile Gly Glu His Gly Thr Ile Leu Ala Arg Phe Gln Glu
        1075                1080                1085

Ala Leu Asp Arg Ala Tyr Thr Gln Leu Glu Ser Arg Asn Leu Leu His
    1090                1095                1100

Asn Gly His Phe Thr Thr Asp Thr Ala Asn Trp Thr Ile Glu Gly Asp
1105                1110                1115                1120

Ala His His Thr Ile Leu Glu Asp Gly Arg Arg Val Leu Arg Leu Pro
            1125                1130                1135

Asp Trp Ser Ser Asn Ala Thr Gln Thr Ile Glu Ile Glu Asp Phe Asp
        1140                1145                1150

Leu Asp Gln Glu Tyr Gln Leu Leu Ile His Ala Lys Gly Lys Gly Ser
        1155                1160                1165

Ile Thr Leu Gln His Gly Glu Glu Asn Glu Tyr Val Glu Thr His Thr
    1170                1175                1180

His His Thr Asn Asp Phe Ile Thr Ser Gln Asn Ile Pro Phe Thr Phe
1185                1190                1195                1200

Lys Gly Asn Gln Ile Glu Val His Ile Thr Ser Glu Asp Gly Glu Phe
            1205                1210                1215

Leu Ile Asp His Ile Thr Val Ile Glu Val Ser Lys Thr Asp Thr Asn
        1220                1225                1230
```

-continued

Thr Asn Ile Ile Glu Asn Ser Pro Ile Asn Thr Ser Met Asn Ser Asn
    1235                1240               1245

Val Arg Val Asp Ile Pro Arg Ser Leu
    1250            1255

<210> SEQ ID NO 7
<211> LENGTH: 1425
<212> TYPE: DNA
<213> ORGANISM: Bacillus thuringiensis

<400> SEQUENCE: 7

| | | | | |
|---|---|---|---|---|
| atgattattg ataqtaaaac gactttacct agacattcac ttattcatac aattaaatta | 60 |
| aattctaata agaaatatgg tcctggtgat atgactaatg gaaatcaatt tattatttca | 120 |
| aaacaagaat gggctacgat tggagcatat attcagactg gattaggttt accagtaaat | 180 |
| gaacaacaat taagaacaca tgttaattta agtcaggata tatcaatacc tagtgatttt | 240 |
| tctcaattat atgatgttta ttgttctgat aaaacttcag cagaatggtg gaataaaaat | 300 |
| ttatatcctt taattattaa atctgctaat gatattgctt catatggttt taagttgct | 360 |
| ggtgatcctt ctattaagaa agatggatat tttaaaaaat tgcaagatga attagataat | 420 |
| attgttgata taattccga tgatgatgca atagctaaag ctattaaaga ttttaaagcg | 480 |
| cgatgtggta ttttaattaa agaagctaaa caatatgaag aagctgcaaa aaatattgta | 540 |
| acatctttag atcaattttt acatggtgat cagaaaaaat tagaaggtgt tatcaatatt | 600 |
| caaaaacgtt taaagaagt tcaaacagct cttaatcaag cccatgggga agtagtcca | 660 |
| gctcataaag agttattaga aaagtaaaa aatttaaaaa caacattaga aaggactat | 720 |
| aaagctgaac aagatttaga gaaaaagta gaatatagtt ttctattagg accattgtta | 780 |
| ggatttgttg tttatgaaat tcttgaaaat actgctgttc agcatataaa aaatcaaatt | 840 |
| gatgagataa agaaacaatt agattctgct cagcatgatt ggatagaga tgttaaaatt | 900 |
| ataggaatgt taaatagtat taatacagat attgataatt tatatagtca aggacaagaa | 960 |
| gcaattaaag ttttccaaaa gttacaaggt atttgggcta ctattggagc tcaaatagaa | 1020 |
| aatcttagaa caacgtcgtt acaagaagtt caagattctg atgatgctga tgagatacaa | 1080 |
| attgaacttg aggacgcttc tgatgcttgg ttagttgtgg ctcaagaagc tcgtgatttt | 1140 |
| acactaaatg cttattcaac taatagtaga caaaatttac cgattaatgt tatatcagat | 1200 |
| tcatgtaatt gttcaacaac aaatatgaca tcaaatcaat acagtaatcc aacaacaaat | 1260 |
| atgcatcaa atcaatatat gatttcacat gaatatacaa gtttaccaaa taattttatg | 1320 |
| ttatcaagaa atagtaattt agaatataaa tgtcctgaaa ataattttat gatatattgg | 1380 |
| tataataatt cggattggta taataattcg gattggtata ataat | 1425 |

<210> SEQ ID NO 8
<211> LENGTH: 475
<212> TYPE: PRT
<213> ORGANISM: Bacillus thuringiensis

<400> SEQUENCE: 8

Met Ile Ile Asp Ser Lys Thr Thr Leu Pro Arg His Ser Leu Ile His
  1               5                  10                  15

Thr Ile Lys Leu Asn Ser Asn Lys Lys Tyr Gly Pro Gly Asp Met Thr
                 20                  25                  30

Asn Gly Asn Gln Phe Ile Ile Ser Lys Gln Glu Trp Ala Thr Ile Gly
             35                  40                  45

```
Ala Tyr Ile Gln Thr Gly Leu Gly Leu Pro Val Asn Glu Gln Gln Leu
 50                  55                  60

Arg Thr His Val Asn Leu Ser Gln Asp Ile Ser Ile Pro Ser Asp Phe
 65                  70                  75                  80

Ser Gln Leu Tyr Asp Val Tyr Cys Ser Asp Lys Thr Ser Ala Glu Trp
             85                  90                  95

Trp Asn Lys Asn Leu Tyr Pro Leu Ile Ile Lys Ser Ala Asn Asp Ile
            100                 105                 110

Ala Ser Tyr Gly Phe Lys Val Ala Gly Asp Pro Ser Ile Lys Lys Asp
            115                 120                 125

Gly Tyr Phe Lys Lys Leu Gln Asp Glu Leu Asp Asn Ile Val Asp Asn
        130                 135                 140

Asn Ser Asp Asp Asp Ala Ile Ala Lys Ala Ile Lys Asp Phe Lys Ala
145                 150                 155                 160

Arg Cys Gly Ile Leu Ile Lys Glu Ala Lys Gln Tyr Glu Glu Ala Ala
                165                 170                 175

Lys Asn Ile Val Thr Ser Leu Asp Gln Phe Leu His Gly Asp Gln Lys
            180                 185                 190

Lys Leu Glu Gly Val Ile Asn Ile Gln Lys Arg Leu Lys Glu Val Gln
        195                 200                 205

Thr Ala Leu Asn Gln Ala His Gly Glu Ser Ser Pro Ala His Lys Glu
    210                 215                 220

Leu Leu Glu Lys Val Lys Asn Leu Lys Thr Thr Leu Glu Arg Thr Ile
225                 230                 235                 240

Lys Ala Glu Gln Asp Leu Glu Lys Lys Val Glu Tyr Ser Phe Leu Leu
                245                 250                 255

Gly Pro Leu Leu Gly Phe Val Val Tyr Glu Ile Leu Glu Asn Thr Ala
            260                 265                 270

Val Gln His Ile Lys Asn Gln Ile Asp Glu Ile Lys Lys Gln Leu Asp
        275                 280                 285

Ser Ala Gln His Asp Leu Asp Arg Asp Val Lys Ile Ile Gly Met Leu
    290                 295                 300

Asn Ser Ile Asn Thr Asp Ile Asp Asn Leu Tyr Ser Gln Gly Gln Glu
305                 310                 315                 320

Ala Ile Lys Val Phe Gln Lys Leu Gln Gly Ile Trp Ala Thr Ile Gly
                325                 330                 335

Ala Gln Ile Glu Asn Leu Arg Thr Thr Ser Leu Gln Glu Val Gln Asp
            340                 345                 350

Ser Asp Asp Ala Asp Glu Ile Gln Ile Glu Leu Glu Asp Ala Ser Asp
        355                 360                 365

Ala Trp Leu Val Val Ala Gln Glu Ala Arg Asp Phe Thr Leu Asn Ala
    370                 375                 380

Tyr Ser Thr Asn Ser Arg Gln Asn Leu Pro Ile Asn Val Ile Ser Asp
385                 390                 395                 400

Ser Cys Asn Cys Ser Thr Thr Asn Met Thr Ser Asn Gln Tyr Ser Asn
                405                 410                 415

Pro Thr Thr Asn Met Thr Ser Asn Gln Tyr Met Ile Ser His Glu Tyr
            420                 425                 430

Thr Ser Leu Pro Asn Asn Phe Met Leu Ser Arg Asn Ser Asn Leu Glu
        435                 440                 445

Tyr Lys Cys Pro Glu Asn Asn Phe Met Ile Tyr Trp Tyr Asn Asn Ser
    450                 455                 460
```

-continued

Asp Trp Tyr Asn Asn Ser Asp Trp Tyr Asn Asn
465 470 475

<210> SEQ ID NO 9
<211> LENGTH: 1185
<212> TYPE: DNA
<213> ORGANISM: Bacillus thuringiensis

<400> SEQUENCE: 9
atgattttag ggaatggaaa gactttacca aagcatataa gattagctca tatttttgca 60
acacagaatt cttcagctaa gaaagacaat cctcttggac cagaggggat ggttactaaa 120
gacggtttta taatctctaa ggaagaatgg gcatttgtgc aggcctatgt gactacaggc 180
actggtttac ctatcaatga cgatgagatg cgtagacatg ttgggttacc atcacgcatt 240
caaattcctg atgattttaa tcaattatat aaggtttata atgaagataa acatttatgc 300
agttggtgga atggtttctt gtttccatta gttcttaaaa cagctaatga tatttccgct 360
tacggattta aatgtgctgg aaagggtgcc actaaaggat attatgaggt catgcaagac 420
gatgtagaaa atatttcaga taatggttat gataaagttg cacaagaaaa agcacataag 480
gatctgcagg cgcgttgtaa aatccttatt aaggaggctg atcaatataa agctgcagcg 540
gatgatgttt caaaacattt aaacacattt cttaaaggcg gtcaagattc agatggcaat 600
gatgttattg gcgtagaggc tgttcaagta caactagcac aagtaaaaga taatcttgat 660
ggcctatatg gcgacaaaag cccaagacat gaagagttac taaagaaagt agacgacctg 720
aaaaaagagt tggaagctgc tattaaagca gagaatgaat tagaaaagaa agtgaaaatg 780
agttttgctt taggaccatt acttggattt gttgtatatg aaatcttaga gctaactgcg 840
gtcaaaagta tacacaagaa agttgaggca ctacaagccg agcttgacac tgctaatgat 900
gaactcgaca gagatgtaaa aatcttagga atgatgaata gcattgacac tgatattgac 960
aacatgttag agcaaggtga gcaagctctt gttgtattta gaaaaattgc aggcatttgg 1020
agtgttataa gtcttaatat cggcaatctt cgagaaacat ctttaaaaga gatagaagaa 1080
gaaaatgatg acgatgcact gtatattgag cttggtgatg ccgctggtca atggaaagag 1140
atagccgagg aggcacaatc ctttgtacta aatgcttata ctcct 1185

<210> SEQ ID NO 10
<211> LENGTH: 395
<212> TYPE: PRT
<213> ORGANISM: Bacillus thuringiensis

<400> SEQUENCE: 10

Met Ile Leu Gly Asn Gly Lys Thr Leu Pro Lys His Ile Arg Leu Ala
1 5 10 15

His Ile Phe Ala Thr Gln Asn Ser Ser Ala Lys Lys Asp Asn Pro Leu
20 25 30

Gly Pro Glu Gly Met Val Thr Lys Asp Gly Phe Ile Ile Ser Lys Glu
35 40 45

Glu Trp Ala Phe Val Gln Ala Tyr Val Thr Thr Gly Thr Gly Leu Pro
50 55 60

Ile Asn Asp Asp Glu Met Arg Arg His Val Gly Leu Pro Ser Arg Ile
65 70 75 80

Gln Ile Pro Asp Asp Phe Asn Gln Leu Tyr Lys Val Tyr Asn Glu Asp
85 90 95

Lys His Leu Cys Ser Trp Trp Asn Gly Phe Leu Phe Pro Leu Val Leu
100 105 110

-continued

```
Lys Thr Ala Asn Asp Ile Ser Ala Tyr Gly Phe Lys Cys Ala Gly Lys
        115                 120                 125

Gly Ala Thr Lys Gly Tyr Tyr Glu Val Met Gln Asp Asp Val Glu Asn
    130                 135                 140

Ile Ser Asp Asn Gly Tyr Asp Lys Val Ala Gln Glu Lys Ala His Lys
145                 150                 155                 160

Asp Leu Gln Ala Arg Cys Lys Ile Leu Ile Lys Glu Ala Asp Gln Tyr
                165                 170                 175

Lys Ala Ala Ala Asp Asp Val Ser Lys His Leu Asn Thr Phe Leu Lys
            180                 185                 190

Gly Gly Gln Asp Ser Asp Gly Asn Asp Val Ile Gly Val Glu Ala Val
        195                 200                 205

Gln Val Gln Leu Ala Gln Val Lys Asp Asn Leu Asp Gly Leu Tyr Gly
    210                 215                 220

Asp Lys Ser Pro Arg His Glu Glu Leu Leu Lys Lys Val Asp Asp Leu
225                 230                 235                 240

Lys Lys Glu Leu Glu Ala Ala Ile Lys Ala Glu Asn Glu Leu Glu Lys
                245                 250                 255

Lys Val Lys Met Ser Phe Ala Leu Gly Pro Leu Leu Gly Phe Val Val
            260                 265                 270

Tyr Glu Ile Leu Glu Leu Thr Ala Val Lys Ser Ile His Lys Lys Val
        275                 280                 285

Glu Ala Leu Gln Ala Glu Leu Asp Thr Ala Asn Asp Glu Leu Asp Arg
    290                 295                 300

Asp Val Lys Ile Leu Gly Met Met Asn Ser Ile Asp Thr Asp Ile Asp
305                 310                 315                 320

Asn Met Leu Glu Gln Gly Glu Gln Ala Leu Val Val Phe Arg Lys Ile
                325                 330                 335

Ala Gly Ile Trp Ser Val Ile Ser Leu Asn Ile Gly Asn Leu Arg Glu
            340                 345                 350

Thr Ser Leu Lys Glu Ile Glu Glu Glu Asn Asp Asp Asp Ala Leu Tyr
        355                 360                 365

Ile Glu Leu Gly Asp Ala Ala Gly Gln Trp Lys Glu Ile Ala Glu Glu
    370                 375                 380

Ala Gln Ser Phe Val Leu Asn Ala Tyr Thr Pro
385                 390                 395
```

<210> SEQ ID NO 11
<211> LENGTH: 2412
<212> TYPE: DNA
<213> ORGANISM: Bacillus thuringiensis

<400> SEQUENCE: 11

```
atgacttgtc aattacaagc gcaaccactt attccctata acgtactagc aggagttcca      60
actagtaata caggtagtcc aatcggcaat gcaggtaatc aatttgatca gtttgagcaa     120
accgttaaag agctcaagga agcatgggaa gcgttccaaa aaaacggaag tttctcatta     180
gcagctcttg aaaagggatt tgatgcagca atcggaggag gatcctttga ttatttaggt     240
ttagttcaag ccggcctagg attagttggt acgctaggcg ccgcaatccc tggtgtttca     300
gtggcagtgc ctcttattag catgcttgtt ggtgtttttt ggccaaaggg cacaaacaac     360
caagaaaacc ttattacagt tattgataag gaagttcaga gaatactaga tgaaaagcta     420
tctgatcagt taataaagaa attgaacgca gatttaaatg cttttacgga cctagtaact     480
```

-continued

```
cgtttggaag aagtaataat agatgcaact ttcgagaatc acaagcctgt actacaagta      540
agtaaatcaa attatatgaa agtggattca gcatatttct caacaggagg tattcttact      600
cttggcatga gtgattttct tactgatacc tattcaaagc ttaccttccc attatatgta      660
ctaggcgcaa ctatgaaact ttcagcatat catagttata caattcgg aaatacatgg        720 cttaataaag tttatgattt atcatcagat gagggaaaaa caatgtcgca ggctttagca      780
cgagctaaac agcatatgcg ccaagacata gcattttata caagccaagc tttaaacatg      840
tttactggga atctcccttc attatcatct aataaatatg caattaatga ctataatgta      900
tacactcgag caatggtatt gaatggctta gatatagtag caacatggcc tacactatat      960
ccagatgact attcgtctca gataaaactg gagaaaacac gcgtgatctt ttcagatatg     1020
gtcgggcaaa gtgagagtag agatggcagc gtaacgatta aaaatatttt tgacaataca     1080
gattcacatc aacatggatc cataggtctc aattcaatct cttatttccc agatgagtta     1140
cagaaagcac aacttcgcat gtatgattat aatcacaaac cttattgtac ggactgtttc     1200
tgctggccgt atggagtgat tttaaactat aacaagaata cctttagata tggcgataat     1260
gatccaggtc tttcaggaga cgttcaactc ccagcaccta tgagtgtagt taatgcccaa     1320
actcaaacag cccaatatac agatggagaa acatatggaa cagatactgg ccgcagttgg     1380
ctttgtactc tacgtggcta ctgtactaca aactgttttc caggaagagg ttgttataat     1440
aatagtactg gatatggaga agttgcaat caatcacttc caggtcaaaa aatacatgca      1500
ctatatcctt ttacacaaac aaatgtgctg gacaatcag gcaaactagg attgctagca     1560
agtcatattc catatgacct aagtccgaac aatacgattg gtgacaaaga tacgattct      1620 acgaatattg tcgcaaaagg aattccagtg gaaaagggt atgcatccag tggacaaaaa      1680
gttgaaatta tacgagagtg gataaatggt gcgaatgtag ttcaattatc tccaggccaa     1740
tcttggggaa tggattttac caatagcaca ggtggtcaat atatggtccg ctgtcgatat     1800
gcaagtacaa acgatactcc aatcttttt aatttagtgt atgacgggg atcgaatcct       1860 atttataacc agatgacatt ccctgctaca aaagagactc cagctcacga ttcagtagat     1920
aacaagatac taggcataaa aggaataaat ggaaattatt cactcatgaa tgtaaaagat     1980
tctgtcgaac ttccatctgg gaatttcat gtttttttca caaataatgg atcatctgct      2040
atttatttag atcgacttga gtttgttcct ttagatcaac cagcagcgcc aacacagtca     2100
acacaaccaa ttaattatcc tatcacaagt aggttacctc atcgttccgg agaaccacct     2160
gcaataatat gggagaaatc agggaatgtt cgcgggaatc aactaactat atcggcacaa     2220
ggtgttccag aaaattccca aatatatctt tcggtgggtg gcgatcgcca aattttagac     2280
cgtagcaacg gatttaaatt agttaattac tcacctactt attctttcac taacattcag     2340
gctagctcgt caaatttagt agatattaca agtggtacca tcactggcca agtacaagta     2400
tctaatctat aa                                                         2412
```

```
<210> SEQ ID NO 12
<211> LENGTH: 803
<212> TYPE: PRT
<213> ORGANISM: Bacillus thuringiensis

<400> SEQUENCE: 12

Met Thr Cys Gln Leu Gln Ala Gln Pro Leu Ile Pro Tyr Asn Val Leu
  1               5                  10                  15

Ala Gly Val Pro Thr Ser Asn Thr Gly Ser Pro Ile Gly Asn Ala Gly
             20                  25                  30
```

```
Asn Gln Phe Asp Gln Phe Glu Gln Thr Val Lys Glu Leu Lys Glu Ala
         35                  40                  45
Trp Glu Ala Phe Gln Lys Asn Gly Ser Phe Ser Leu Ala Ala Leu Glu
 50                  55                  60
Lys Gly Phe Asp Ala Ala Ile Gly Gly Ser Phe Asp Tyr Leu Gly
 65                  70                  75                  80
Leu Val Gln Ala Gly Leu Gly Leu Val Gly Thr Leu Gly Ala Ala Ile
                 85                  90                  95
Pro Gly Val Ser Val Ala Val Pro Leu Ile Ser Met Leu Val Gly Val
                100                 105                 110
Phe Trp Pro Lys Gly Thr Asn Asn Gln Glu Asn Leu Ile Thr Val Ile
             115                 120                 125
Asp Lys Glu Val Gln Arg Ile Leu Asp Glu Lys Leu Ser Asp Gln Leu
130                 135                 140
Ile Lys Lys Leu Asn Ala Asp Leu Asn Ala Phe Thr Asp Leu Val Thr
145                 150                 155                 160
Arg Leu Glu Glu Val Ile Ile Asp Ala Thr Phe Glu Asn His Lys Pro
                165                 170                 175
Val Leu Gln Val Ser Lys Ser Asn Tyr Met Lys Val Asp Ser Ala Tyr
                180                 185                 190
Phe Ser Thr Gly Gly Ile Leu Thr Leu Gly Met Ser Asp Phe Leu Thr
             195                 200                 205
Asp Thr Tyr Ser Lys Leu Thr Phe Pro Leu Tyr Val Leu Gly Ala Thr
210                 215                 220
Met Lys Leu Ser Ala Tyr His Ser Tyr Ile Gln Phe Gly Asn Thr Trp
225                 230                 235                 240
Leu Asn Lys Val Tyr Asp Leu Ser Ser Asp Glu Gly Lys Thr Met Ser
                245                 250                 255
Gln Ala Leu Ala Arg Ala Lys Gln His Met Arg Gln Asp Ile Ala Phe
             260                 265                 270
Tyr Thr Ser Gln Ala Leu Asn Met Phe Thr Gly Asn Leu Pro Ser Leu
275                 280                 285
Ser Ser Asn Lys Tyr Ala Ile Asn Asp Tyr Asn Val Tyr Thr Arg Ala
290                 295                 300
Met Val Leu Asn Gly Leu Asp Ile Val Ala Thr Trp Pro Thr Leu Tyr
305                 310                 315                 320
Pro Asp Asp Tyr Ser Ser Gln Ile Lys Leu Glu Lys Thr Arg Val Ile
                325                 330                 335
Phe Ser Asp Met Val Gly Gln Ser Glu Ser Arg Asp Gly Ser Val Thr
             340                 345                 350
Ile Lys Asn Ile Phe Asp Asn Thr Asp Ser His Gln His Gly Ser Ile
             355                 360                 365
Gly Leu Asn Ser Ile Ser Tyr Phe Pro Asp Glu Leu Gln Lys Ala Gln
370                 375                 380
Leu Arg Met Tyr Asp Tyr Asn His Lys Pro Tyr Cys Thr Asp Cys Phe
385                 390                 395                 400
Cys Trp Pro Tyr Gly Val Ile Leu Asn Tyr Asn Lys Asn Thr Phe Arg
                405                 410                 415
Tyr Gly Asp Asn Asp Pro Gly Leu Ser Gly Asp Val Gln Leu Pro Ala
                420                 425                 430
Pro Met Ser Val Val Asn Ala Gln Thr Gln Thr Ala Gln Tyr Thr Asp
             435                 440                 445
```

```
Gly Glu Asn Ile Trp Thr Asp Thr Gly Arg Ser Trp Leu Cys Thr Leu
    450                 455                 460

Arg Gly Tyr Cys Thr Thr Asn Cys Phe Pro Gly Arg Gly Cys Tyr Asn
465                 470                 475                 480

Asn Ser Thr Gly Tyr Gly Glu Ser Cys Asn Gln Ser Leu Pro Gly Gln
                485                 490                 495

Lys Ile His Ala Leu Tyr Pro Phe Thr Gln Thr Asn Val Leu Gly Gln
            500                 505                 510

Ser Gly Lys Leu Gly Leu Leu Ala Ser His Ile Pro Tyr Asp Leu Ser
        515                 520                 525

Pro Asn Asn Thr Ile Gly Asp Lys Asp Thr Asp Ser Thr Asn Ile Val
    530                 535                 540

Ala Lys Gly Ile Pro Val Glu Lys Gly Tyr Ala Ser Ser Gly Gln Lys
545                 550                 555                 560

Val Glu Ile Ile Arg Glu Trp Ile Asn Gly Ala Asn Val Val Gln Leu
                565                 570                 575

Ser Pro Gly Gln Ser Trp Gly Met Asp Phe Thr Asn Ser Thr Gly Gly
            580                 585                 590

Gln Tyr Met Val Arg Cys Arg Tyr Ala Ser Thr Asn Asp Thr Pro Ile
        595                 600                 605

Phe Phe Asn Leu Val Tyr Asp Gly Gly Ser Asn Pro Ile Tyr Asn Gln
    610                 615                 620

Met Thr Phe Pro Ala Thr Lys Glu Thr Pro Ala His Asp Ser Val Asp
625                 630                 635                 640

Asn Lys Ile Leu Gly Ile Lys Gly Ile Asn Gly Asn Tyr Ser Leu Met
                645                 650                 655

Asn Val Lys Asp Ser Val Glu Leu Pro Ser Gly Lys Phe His Val Phe
            660                 665                 670

Phe Thr Asn Asn Gly Ser Ser Ala Ile Tyr Leu Asp Arg Leu Glu Phe
        675                 680                 685

Val Pro Leu Asp Gln Pro Ala Ala Pro Thr Gln Ser Thr Gln Pro Ile
    690                 695                 700

Asn Tyr Pro Ile Thr Ser Arg Leu Pro His Arg Ser Gly Glu Pro Pro
705                 710                 715                 720

Ala Ile Ile Trp Glu Lys Ser Gly Asn Val Arg Gly Asn Gln Leu Thr
                725                 730                 735

Ile Ser Ala Gln Gly Val Pro Glu Asn Ser Gln Ile Tyr Leu Ser Val
            740                 745                 750

Gly Gly Asp Arg Gln Ile Leu Asp Arg Ser Asn Gly Phe Lys Leu Val
        755                 760                 765

Asn Tyr Ser Pro Thr Tyr Ser Phe Thr Asn Ile Gln Ala Ser Ser Ser
    770                 775                 780

Asn Leu Val Asp Ile Thr Ser Gly Thr Ile Thr Gly Gln Val Gln Val
785                 790                 795                 800

Ser Asn Leu

<210> SEQ ID NO 13
<211> LENGTH: 8
<212> TYPE: PRT
<213> ORGANISM: probe

<400> SEQUENCE: 13

Arg Glu Trp Ile Asn Gly Ala Asn
  1               5
```

<210> SEQ ID NO 14
<211> LENGTH: 22
<212> TYPE: DNA
<213> ORGANISM: probe

<400> SEQUENCE: 14
agartrkwtw aatggwgckm aw                                              22

<210> SEQ ID NO 15
<211> LENGTH: 8
<212> TYPE: PRT
<213> ORGANISM: probe

<400> SEQUENCE: 15

Pro Thr Phe Asp Pro Asp Leu Tyr
 1               5

<210> SEQ ID NO 16
<211> LENGTH: 24
<212> TYPE: DNA
<213> ORGANISM: probe

<400> SEQUENCE: 16
ccnacytttk atccagatsw ytat                                            24

<210> SEQ ID NO 17
<211> LENGTH: 14
<212> TYPE: PRT
<213> ORGANISM: Bacillus thuringiensis

<400> SEQUENCE: 17

Ala Ile Leu Asn Glu Leu Tyr Pro Ser Val Pro Tyr Asn Val
 1               5                  10

<210> SEQ ID NO 18
<211> LENGTH: 14
<212> TYPE: PRT
<213> ORGANISM: Bacillus thuringiensis

<400> SEQUENCE: 18

Ala Ile Leu Asn Glu Leu Tyr Pro Ser Val Pro Tyr Asn Val
 1               5                  10

<210> SEQ ID NO 19
<211> LENGTH: 17
<212> TYPE: PRT
<213> ORGANISM: Bacillus thuringiensis

<400> SEQUENCE: 19

Met Ile Ile Asp Ser Lys Thr Thr Leu Pro Arg His Ser Leu Ile Asn
 1               5                  10                  15

Thr

<210> SEQ ID NO 20
<211> LENGTH: 14
<212> TYPE: PRT
<213> ORGANISM: Bacillus thuringiensis

<400> SEQUENCE: 20

Gln Leu Gln Ala Gln Pro Leu Ile Pro Tyr Asn Val Leu Ala
 1               5                  10

<210> SEQ ID NO 21

-continued

<211> LENGTH: 24
<212> TYPE: PRT
<213> ORGANISM: Bacillus thuringiensis

<400> SEQUENCE: 21

```
Met Ile Leu Gly Asn Gly Lys Thr Leu Pro Lys His Ile Arg Leu Ala
  1               5                  10                  15

His Ile Phe Ala Thr Gln Asn Ser
             20
```

<210> SEQ ID NO 22
<211> LENGTH: 10
<212> TYPE: PRT
<213> ORGANISM: Bacillus thuringiensis

<400> SEQUENCE: 22

```
Ala Thr Leu Asn Glu Val Tyr Pro Val Asn
  1               5                  10
```

<210> SEQ ID NO 23
<211> LENGTH: 15
<212> TYPE: PRT
<213> ORGANISM: Bacillus thuringiensis

<400> SEQUENCE: 23

```
Val Gln Arg Ile Leu Asp Glu Lys Leu Ser Phe Gln Leu Ile Lys
  1               5                  10                  15
```

<210> SEQ ID NO 24
<211> LENGTH: 23
<212> TYPE: DNA
<213> ORGANISM: Artificial Sequence
<220> FEATURE:
<223> OTHER INFORMATION: Description of Artificial Sequence:
Synthetic oligonucleotide

<400> SEQUENCE: 24

```
gcaattttaa atgaattata tcc                                              23
```

<210> SEQ ID NO 25
<211> LENGTH: 56
<212> TYPE: DNA
<213> ORGANISM: Artificial Sequence
<220> FEATURE:
<223> OTHER INFORMATION: Description of Artificial Sequence:
Oligonucleotide probe

<400> SEQUENCE: 25

```
atgattattg attctaaaac aacattacca agacattcwt taatwaatac watwaa         56
```

<210> SEQ ID NO 26
<211> LENGTH: 38
<212> TYPE: DNA
<213> ORGANISM: Artificial Sequence
<220> FEATURE:
<223> OTHER INFORMATION: Description of Artificial Sequence:Synthetic
oligonucleotide probe

<400> SEQUENCE: 26

```
aaacatatta gattagcaca tatttttgca acacaaaa                             38
```

<210> SEQ ID NO 27
<211> LENGTH: 17
<212> TYPE: DNA
<213> ORGANISM: Artificial Sequence
<220> FEATURE:

-continued

```
<223> OTHER INFORMATION: Description of Artificial Sequence:forward
      primer

<400> SEQUENCE: 27
caaytacaag cwcaacc                                                      17

<210> SEQ ID NO 28
<211> LENGTH: 21
<212> TYPE: DNA
<213> ORGANISM: Artificial Sequence
<220> FEATURE:
<223> OTHER INFORMATION: Description of Artificial Sequence:reverse
      primer

<400> SEQUENCE: 28
ttcatctaaa attctttgwa c                                                 21

<210> SEQ ID NO 29
<211> LENGTH: 8
<212> TYPE: PRT
<213> ORGANISM: Artificial Sequence
<220> FEATURE:
<223> OTHER INFORMATION: Description of Artificial Sequence:Nematode
      variant of region 5 of Hofte and Whiteley

<400> SEQUENCE: 29

Leu Asp Arg Ile Gln Phe Ile Pro
  1               5

<210> SEQ ID NO 30
<211> LENGTH: 23
<212> TYPE: DNA
<213> ORGANISM: Artificial Sequence
<220> FEATURE:
<223> OTHER INFORMATION: Description of Artificial Sequence:reverse
      primer

<400> SEQUENCE: 30
aggaacaaay tcaakwcgrt cta                                               23

<210> SEQ ID NO 31
<211> LENGTH: 9
<212> TYPE: PRT
<213> ORGANISM: Artificial Sequence
<220> FEATURE:
<223> OTHER INFORMATION: Description of Artificial Sequence:reverse
      primer

<400> SEQUENCE: 31

Tyr Ile Asp Lys Ile Glu Phe Ile Pro
  1               5

<210> SEQ ID NO 32
<211> LENGTH: 23
<212> TYPE: DNA
<213> ORGANISM: Artificial Sequence
<220> FEATURE:
<223> OTHER INFORMATION: Description of Artificial Sequence:primer

<400> SEQUENCE: 32
tggaataaat tcaattykrt cwa                                               23

<210> SEQ ID NO 33
<211> LENGTH: 21
<212> TYPE: DNA
<213> ORGANISM: Artificial Sequence
<220> FEATURE:
```

```
<223> OTHER INFORMATION: Description of Artificial Sequence:
      oligonucleotide probe

<400> SEQUENCE: 33
gcwacwttaa atgaagtwta t                                              21

<210> SEQ ID NO 34
<211> LENGTH: 21
<212> TYPE: DNA
<213> ORGANISM: Artificial Sequence
<220> FEATURE:
<223> OTHER INFORMATION: Description of Artificial Sequence:oligonucleotide
      probe

<400> SEQUENCE: 34
aatgaagtwt atccwgtwaa t                                              21

<210> SEQ ID NO 35
<211> LENGTH: 38
<212> TYPE: DNA
<213> ORGANISM: Artificial Sequence
<220> FEATURE:
<223> OTHER INFORMATION: Description of Artificial Sequence:reverse primer

<400> SEQUENCE: 35
gcaagcggcc gcttatggaa taaattcaat tykrtcwa                            38

<210> SEQ ID NO 36
<211> LENGTH: 28
<212> TYPE: DNA
<213> ORGANISM: Artificial Sequence
<220> FEATURE:
<223> OTHER INFORMATION: Description of Artificial Sequence:forward primer

<400> SEQUENCE: 36
tgattttwmt caattatatr akgtttat                                       28

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence:probe

<400> SEQUENCE: 37
aagagttayt araraaagta                                                20

<210> SEQ ID NO 38
<211> LENGTH: 35
<212> TYPE: DNA
<213> ORGANISM: Artificial Sequence
<220> FEATURE:
<223> OTHER INFORMATION: Description of Artificial Sequence:probe

<400> SEQUENCE: 38
ttaggaccat trytwggatt tgttgtwtat gaaat                               35

<210> SEQ ID NO 39
<211> LENGTH: 27
<212> TYPE: DNA
<213> ORGANISM: Artificial Sequence
<220> FEATURE:
<223> OTHER INFORMATION: Description of Artificial Sequence:probe

<400> SEQUENCE: 39
gayagagatg twaaaatywt aggaatg                                        27
```

<210> SEQ ID NO 40
<211> LENGTH: 23
<212> TYPE: DNA
<213> ORGANISM: Artificial Sequence
<220> FEATURE:
<223> OTHER INFORMATION: Description of Artificial Sequence:forward
      primer

<400> SEQUENCE: 40
ttmttaaawc wgctaatgat att                                          23

<210> SEQ ID NO 41
<211> LENGTH: 716
<212> TYPE: PRT
<213> ORGANISM: Generic Formula I

<400> SEQUENCE: 41

Met Xaa Xaa Xaa Xaa Xaa Xaa Xaa Pro Xaa Xaa Pro Tyr Asn Xaa Xaa
 1               5                  10                  15

Xaa Xaa Xaa Pro Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Tyr Xaa
 65                  70                  75                  80

Xaa Xaa Val Xaa Xaa Xaa Xaa Xaa Xaa Xaa Xaa Xaa Xaa Xaa
            85                  90                  95

Xaa Pro Xaa Xaa Xaa Xaa Xaa Xaa Pro Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Xaa Xaa Xaa Xaa Xaa
    130                 135                 140

Xaa Xaa Xaa Xaa Xaa Xaa Xaa Xaa Xaa Xaa Xaa Xaa Xaa Xaa Xaa
145                 150                 155                 160

Xaa Xaa Xaa Xaa Xaa Xaa Xaa Xaa Xaa Xaa Xaa Xaa Xaa Xaa Xaa
                165                 170                 175

Xaa His Xaa Xaa Xaa Xaa Xaa Xaa Xaa Xaa Xaa Xaa Xaa Xaa
            180                 185                 190

Xaa Xaa Xaa Xaa Xaa Xaa Xaa Xaa Xaa Xaa Xaa Xaa Xaa Xaa
        195                 200                 205

Xaa Xaa Xaa Xaa Xaa Xaa Xaa Xaa Xaa Xaa Xaa Leu Xaa Xaa Pro
    210                 215                 220

Xaa Tyr Xaa Xaa Xaa Xaa Xaa Met Xaa Xaa Xaa Xaa Xaa Xaa Xaa
225                 230                 235                 240

Xaa Xaa Xaa Xaa Xaa Xaa Xaa Xaa Xaa Xaa Xaa Xaa Xaa Xaa
            245                 250                 255

Xaa Xaa Xaa Xaa Xaa Xaa Xaa Xaa Xaa Xaa Xaa Xaa Xaa Xaa
        260                 265                 270

Xaa Xaa Xaa Xaa Xaa Xaa Xaa Tyr Xaa Xaa Xaa Xaa Xaa Xaa
    275                 280                 285

Xaa Xaa Xaa Xaa Xaa Xaa Xaa Xaa Xaa Xaa Xaa Xaa Xaa Xaa
        290                 295                 300

Xaa Xaa Xaa Xaa Xaa Tyr Xaa Xaa Xaa Met Xaa Xaa Xaa Xaa Xaa
305                 310                315

Xaa Xaa Xaa Xaa Xaa Xaa Xaa Xaa Xaa Pro Xaa Xaa Tyr Xaa Xaa Xaa
            325                     330                 335

Xaa Xaa Xaa Xaa Xaa Xaa Xaa Xaa Xaa Xaa Xaa Xaa Xaa Xaa Xaa
            340                 345                 350

Xaa Xaa Xaa Xaa Xaa Xaa Xaa Xaa Xaa Xaa Xaa Xaa Xaa Xaa Xaa Xaa
            355                 360                 365

Xaa Xaa Xaa Xaa Xaa Xaa Xaa Xaa Xaa Xaa Xaa Xaa Xaa Xaa Xaa
    370                 375                 380

Xaa Xaa Xaa Xaa Xaa Xaa Xaa Xaa Xaa Xaa Xaa Xaa Xaa Xaa Tyr
385                 390                 395                 400

Xaa Xaa Xaa Xaa Xaa Xaa Xaa Xaa Xaa Xaa Xaa Xaa Tyr Xaa
            405                 410                 415

Xaa Xaa Xaa Xaa Xaa Xaa Xaa Xaa Xaa Xaa Xaa Tyr Xaa Xaa
            420                 425             430

Xaa Xaa Xaa Xaa Xaa Pro Xaa Xaa Xaa Xaa Xaa Xaa Xaa Xaa
            435                 440             445

Xaa Xaa Xaa Pro Xaa Xaa Xaa Xaa Xaa Xaa Xaa Xaa Xaa Xaa Xaa
450                 455                 460

Xaa Xaa Xaa Xaa Xaa Xaa Xaa Xaa Xaa Xaa Xaa Xaa Xaa Xaa Xaa Xaa
465                 470                 475                 480

Xaa Xaa Xaa Xaa Xaa Xaa Xaa Xaa Xaa Xaa Xaa Xaa Xaa Xaa Xaa
            485                 490                 495

Xaa Xaa Xaa Xaa Xaa Xaa Xaa Xaa Xaa Xaa Xaa Xaa Xaa Xaa Xaa
            500                 505                 510

Xaa Xaa Xaa Xaa Xaa Xaa Xaa Xaa Xaa Xaa Xaa Xaa Xaa Xaa Xaa
            515                 520                 525

Xaa Xaa Xaa Xaa Xaa Xaa Xaa Xaa Xaa Xaa Xaa Xaa Xaa Xaa Xaa
            530                 535                 540

Xaa Xaa Xaa Pro Xaa Xaa Xaa Xaa Xaa Xaa Xaa Xaa Xaa Xaa Xaa
545                 550                 555                 560

Xaa Xaa Xaa Xaa Xaa Xaa Xaa Xaa Xaa Xaa Xaa Pro Xaa Xaa Xaa
            565                 570                 575

Xaa Xaa Xaa Xaa Xaa Xaa Xaa Xaa Xaa Xaa Xaa Xaa Xaa Trp Leu
            580                 585                 590

Xaa Xaa Xaa Xaa Xaa Xaa Xaa Xaa Pro Xaa Xaa Xaa Xaa Xaa Xaa
            595                 600                 605

Xaa Xaa Xaa Xaa Xaa Xaa Xaa Xaa Tyr Xaa Xaa Arg Cys Arg Tyr
    610                 615                 620

Xaa Xaa Xaa Xaa Xaa Xaa Xaa Xaa Xaa Xaa Xaa Xaa Xaa Xaa Xaa
625                 630                 635                 640

Xaa Xaa Xaa Xaa Xaa Xaa Xaa Xaa Xaa Xaa Xaa Xaa Xaa Xaa Xaa
            645                 650                 655

Xaa Xaa Xaa Xaa Xaa Xaa Xaa Xaa Xaa Xaa Xaa Xaa Xaa Xaa Xaa
            660                 665                 670

Xaa Xaa Xaa Xaa Xaa Xaa Xaa Xaa Xaa Xaa Xaa Xaa Xaa Xaa Xaa
            675                 680                 685

Pro Xaa Xaa Xaa Xaa Xaa Xaa Xaa Xaa Xaa Xaa Xaa Ser Ser Xaa
    690                 695                 700

Xaa Xaa Xaa Asp Xaa Xaa Glu Xaa Xaa Pro Xaa Xaa
705

-continued

```
<210> SEQ ID NO 42
<211> LENGTH: 400
<212> TYPE: PRT
<213> ORGANISM: Generic Formula II

<400> SEQUENCE: 42

Met Xaa Xaa Xaa Xaa Xaa Xaa Xaa Pro Lys His Xaa Xaa Xaa Xaa
  1               5                  10                  15

Xaa Xaa Xaa Xaa Xaa Xaa Xaa Xaa Xaa Xaa Xaa Xaa Xaa Xaa Xaa
                 20                  25                  30

Xaa Pro Xaa Xaa Xaa Xaa Xaa Xaa Xaa Xaa Xaa Xaa Xaa Xaa Xaa
             35                  40                  45

Xaa Trp Xaa Xaa Xaa Xaa Xaa Tyr Xaa Xaa Xaa Xaa Xaa Xaa Pro
         50                  55                  60

Xaa Xaa Xaa Xaa Xaa Xaa Xaa His Xaa Xaa Xaa Xaa Xaa Xaa Xaa
 65                  70                  75                  80

Xaa Xaa Pro Xaa Xaa Xaa Xaa Xaa Tyr Xaa Xaa Tyr Xaa Xaa Xaa
             85                  90                  95

Xaa Xaa Xaa Xaa Xaa Trp Trp Xaa Xaa Xaa Xaa Pro Xaa Xaa Xaa
                100                 105                 110

Xaa Xaa Xaa Xaa Xaa Xaa Xaa Tyr Xaa Xaa Xaa Xaa Xaa Xaa Xaa
            115                 120                 125

Xaa Xaa Lys Xaa Xaa Xaa Xaa Xaa Xaa Xaa Xaa Xaa Xaa Xaa Xaa
        130                 135                 140

Xaa Xaa Xaa Xaa Xaa Xaa Xaa Xaa Xaa Xaa Xaa Xaa Xaa Xaa Xaa
145                 150                 155                 160

Xaa Xaa Xaa Xaa Xaa Xaa Xaa Xaa Xaa Xaa Xaa Xaa Xaa Xaa Xaa
                165                 170                 175

Xaa Tyr Xaa Xaa Xaa Xaa Xaa Xaa Xaa Xaa Xaa Xaa Xaa Xaa Xaa
            180                 185                 190

Xaa Xaa Xaa Xaa Xaa Xaa Xaa Xaa Xaa Xaa Xaa Xaa Xaa Xaa Xaa
            195                 200                 205

Xaa Xaa Xaa Xaa Xaa Xaa Xaa Xaa Xaa Xaa Xaa Xaa Xaa Xaa Xaa
        210                 215                 220

Xaa Xaa Xaa Xaa Xaa Xaa Xaa Xaa Xaa Xaa Xaa Xaa Xaa Xaa Xaa
225                 230                 235                 240

Xaa Xaa Xaa Xaa Xaa Leu Glu Xaa Xaa Xaa Xaa Xaa Xaa Xaa Xaa
                245                 250                 255

Xaa Xaa Xaa Xaa Xaa Xaa Xaa Xaa Xaa Xaa Xaa Xaa Xaa Xaa Xaa
            260                 265                 270

Xaa Xaa Tyr Xaa Xaa Xaa Xaa Xaa Xaa Xaa Xaa Xaa Xaa Xaa Xaa
        275                 280                 285

Xaa Xaa Xaa Xaa Xaa Xaa Xaa Xaa Xaa Xaa Xaa Xaa Xaa Xaa Xaa
    290                 295                 300

Xaa Xaa Xaa Xaa Xaa Xaa Xaa Xaa Xaa Xaa Xaa Xaa Xaa Xaa Xaa
305                 310                 315                 320

Xaa Xaa Xaa Xaa Xaa Xaa Xaa Xaa Xaa Xaa Xaa Xaa Xaa Xaa Xaa
                325                 330                 335

Xaa Xaa Xaa Xaa Xaa Tyr Xaa Xaa Xaa Xaa Xaa Xaa Xaa Xaa Xaa
            340                 345                 350

Xaa Xaa Xaa Xaa Xaa Xaa Xaa Xaa Xaa Xaa Xaa Xaa Xaa Xaa Xaa
            355                 360                 365

Xaa Xaa Xaa Xaa Xaa Xaa Xaa Xaa Xaa Xaa Trp Xaa Xaa Xaa Xaa
        370                 375                 380
```

```
Xaa Xaa Xaa Xaa Xaa Xaa Xaa Xaa Xaa Xaa Tyr Xaa Xaa Xaa Xaa Xaa
385                 390                 395                 400
```